US012544513B2

(12) United States Patent
Bechmann et al.

(10) Patent No.: US 12,544,513 B2
(45) Date of Patent: Feb. 10, 2026

(54) ELECTRONIC SYSTEM FOR A DRUG DELIVERY DEVICE

(71) Applicant: Sanofi, Paris (FR)

(72) Inventors: Soeren Bechmann, Struer (DK); Ole Lemming, Struer (DK); Jan Olesen, Struer (DK)

(73) Assignee: SANOFI, Paris (FR)

( * ) Notice: Subject to any disclaimer, the term of this patent is extended or adjusted under 35 U.S.C. 154(b) by 807 days.

(21) Appl. No.: 18/025,477

(22) PCT Filed: Mar. 25, 2021

(86) PCT No.: PCT/EP2021/057672

§ 371 (c)(1),
(2) Date: Mar. 9, 2023

(87) PCT Pub. No.: WO2021/191329

PCT Pub. Date: Sep. 30, 2021

(65) Prior Publication Data

US 2023/0321358 A1 Oct. 12, 2023

(30) Foreign Application Priority Data

Mar. 27, 2020 (EP) .................................... 20315066
Nov. 16, 2020 (EP) .................................... 20315451
Nov. 20, 2020 (EP) .................................... 20315462

(51) Int. Cl.
*A61M 5/315* (2006.01)

(52) U.S. Cl.
CPC .............................. *A61M 5/31568* (2013.01)

(58) Field of Classification Search
CPC ............ A61M 5/31568; A61M 5/3157; A61M 2205/3317; A61M 2205/8212
See application file for complete search history.

(56) References Cited

U.S. PATENT DOCUMENTS 6,236,002 B1 * 5/2001 Chou ................... H01H 19/585 200/11 R
2020/0078527 A1 * 3/2020 Biederman ....... A61M 5/31586
2021/0330891 A1 * 10/2021 Byerly .............. A61M 5/31551

FOREIGN PATENT DOCUMENTS

EP 2729202 5/2018
EP 2890435 3/2020
(Continued)

OTHER PUBLICATIONS

International Preliminary Report on Patentability in International Appln. No. PCT/EP2021/057672, mailed on Oct. 6, 2022, 7 pages.
(Continued)

*Primary Examiner* — Dung T Ulsh
(74) *Attorney, Agent, or Firm* — Bond, Schoeneck & King, PLLC

(57) ABSTRACT

A switch assembly comprising a chassis supporting a PCBA which has a distal surface comprising at least a first, a second, and a third electrical contacts, a ring having a ratchet profile, and a first arm and a second arm. The chassis moves axially relative to the ring during a first switch operation mode. The ring rotates relative to the chassis during a second switch operation mode. An axial movement of the chassis towards the ring closes an electrical connection between the first electrical contact and the first arm. Further, the ratchet profile of the ring is located facing proximally towards the distal surface of the PCBA such that an actuator guided on the ratchet profile elastically deforms the second arm thereby alternately opening and closing an electrical connection between the second electrical contact and the third electrical contact via the second arm.

20 Claims, 11 Drawing Sheets

(56) References Cited

FOREIGN PATENT DOCUMENTS

| | | |
|---|---|---|
| EP | 20315066.9 | 3/2020 |
| EP | 20315357.2 | 7/2020 |
| WO | WO 2014/033195 | 3/2014 |
| WO | WO 2015/028439 | 3/2015 |
| WO | WO 2019/040313 | 2/2019 |
| WO | WO 2021/191329 | 9/2021 |

OTHER PUBLICATIONS

International Search Report and Written Opinion in International Appln. No. PCT/EP2021/057672, mailed on May 10, 2021, 8 pages.

* cited by examiner

ELECTRONIC SYSTEM FOR A DRUG DELIVERY DEVICE

CROSS REFERENCE TO RELATED APPLICATIONS

The present application is the national stage entry of International Patent Application No. PCT/EP2021/057672, filed on Mar. 25, 2021, and claims priority to Application No. EP 20315066.9, filed on Mar. 27, 2020, Application No. EP 20315451.3, filed on Nov. 16, 2020, and Application No. EP 20315462.0, filed on Nov. 20, 2020, the disclosures of which are incorporated herein by reference.

TECHNICAL FIELD

The present disclosure is generally directed to an electronic system for a drug delivery device. The present disclosure further relates to a drug delivery device, which comprises an electronic system.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for disposable and reusable devices.

For such devices the functionality of recording doses that are dialed and delivered from the pen may be of value to a wide variety of device users as a memory aid or to support detailed logging of dose history. Thus, drug delivery devices using electronics are becoming increasingly popular in the pharmaceutical industry as well as for users or patients. For example, a drug delivery device is known from EP 2 729 202 B1 comprising an electronically controlled capturing system for capturing data related to the amount of drug expelled from a reservoir by expelling means.

However, especially if the device is designed to be self-contained, that is to say without a connector for a connection to an electrical power source which is necessary to provide electrical power for the operation of the device, the management of the resources of a power supply integrated into the device is particularly important.

Unpublished EP20315066.9 and EP20315357.2 disclose advantageous embodiments of electronic systems for drug delivery devices with improved power management. These electronic systems comprise a switch assembly for activating/deactivating power consuming functions of the electronic systems.

Such drug delivery devices are typically manufactured in large scale such that an efficient and simple assembly is an important issue to keep production costs reasonably low.

SUMMARY

The present disclosure provides improvements for drug delivery devices comprising an electronic system, and for electronic systems for drug delivery devices allowing reliable activation/deactivation of functions of the electronic system as well as an efficient assembly.

One aspect of the disclosure relates to a switch assembly for an electronic system of a drug delivery device. The switch assembly comprises a chassis supporting a PCBA which has a distal surface comprising at least a first electrical contact, a second electrical contact and a third electrical contact. The switch assembly further comprises a ring having an annular ratchet profile. Still further, the switch assembly comprises, a first electrically conductive and elastically deformable arm and a second electrically conductive and elastically deformable arm. Preferably, the chassis and the ring are arranged and adapted such that the chassis moves axially relative to the ring from a first, e.g. more distant, axial position to a second, e.g. closer, axial position during a first switch operation mode, e.g. during the transition from the dose setting operation to the dose delivery operation of the drug delivery device or when the chassis is pressed in a 0U dialed condition of the drug delivery device. Further, the chassis and the ring are configured such that the ring rotates relative to the chassis during a second switch operation mode, e.g. during the dose delivery operation of the drug delivery device. A reliable switching in both switching modes may be obtained if the first arm is arranged such that axial movement of the chassis towards the ring during the first switch operation mode closes an electrical connection between the first electrical contact and the first arm, and if the ratchet profile of the ring is located facing proximally towards the distal surface of the PCBA such that an actuator guided on the ratchet profile at least during the second switch operation mode elastically deforms the second arm thereby alternately opening and closing an electrical connection between the second electrical contact and the third electrical contact via the second arm. This arrangement of the switch assembly has the further advantage that the chassis, the PCBA with its contacts at the distal surface, the ring with the annular ratchet profile and the first and second electrically conductive arms may be mounted from the same direction into each other to form the switch assembly. This significantly increases assembly efficiency compared with alternatives requiring mounting of the component parts from different directions.

According to a further aspect of the present disclosure a method for assembling a drug delivery device is provided, the drug delivery device comprising a dose setting and drive mechanism, an electronic system with a switch assembly comprising the chassis, the PCBA with its contacts at the distal surface, the ring with the annular ratchet profile and the first and second electrically conductive arms, wherein these component parts of the drug delivery device are mounted from one single direction into and/or onto each other, preferably mounted from a proximal button end of the drug delivery device towards a distal dispensing end. Some of these component parts may be mounted as a pre-assembled sub-unit which itself may or may not be mounted from the same single direction.

The present disclosure comprises several examples achieving the above mentioned advantages.

According to a first example, the actuator may be a lever having a first end hinged to the chassis and a free second end opposite the first end which contacts the ring, e.g. the ratchet profile of the ring, during the during first and second switch operation modes. Preferably, the lever and the first arm and the second arm are arranged such that one of the arms, e.g. the first arm, is contacted by the lever upon a deflection of the lever at a position closer to the first end of the lever hinged to the chassis whereas the other of the arms, e.g. of the second arm, is contacted by the lever upon a deflection of the lever at a position closer to the free second end of the lever. The lever and the first arm and the second arm are preferably configured such that a small deflection of the lever results in the lever and deflecting the first arm without deflecting the second arm and that a larger deflection of the lever results in the lever deflecting both arms. In an unbiased default position of the lever, i.e. if the actuator at the free a second end of the lever is not in contact with the ring, the lever is preferably only in contact with the first arm or, alternatively, is not in contact with any of the arms.

The free second end of the lever may be axially spaced from the ratchet profile in the first axial position, may contact a bottom section of the ratchet profile and may elastically deflect the first arm in the second axial position and may alternate between contacting bottom sections and peak sections of the ratchet profile and elastically deflect the second arm during the second switch operation mode. In addition, the electrical connection between the first arm and the first electrical contact may be open in the first axial position and closed in the second axial position. The electrical connection between the second arm and the second electrical contact may be open in the first and second axial positions and alternately closed during the second switch operation mode when the free second end of the lever contacts peak sections of the ratchet profile.

The first arm and/or of the second arm may be permanently electrically connected to the third contact. As an alternative, one of the first and the second arm may be electrically connected to the third contact, while the other of the first and the second arm is electrically connected to a fourth contact provided on the distal surface of the PCBA.

With this first example the number of additional component parts required to build the switch assembly is relatively low. For example, in drug delivery devices with an electronic system comprising the ring, the chassis and the PCBA, it is only required to provide the lever which may be a component part unitarily made with the chassis and the first and second arms which may be permanently attached to the PCBA. Thus, it is only required to modify the chassis and the PCBA to provide the switch assembly according to the present disclosure. The low number of additional component parts contributes in making the assembly process highly efficient.

According to a second example, a bridge holding a first electrically conductive spring element and a second electrically conductive spring element may be interposed between the ring and the PCBA such that the spring elements bias the bridge away from the PCBA and towards the ring. Further, the first arm may be a free end of the first spring element and the second arm may be a free end of the second spring element. Preferably, at least one of the first spring element and the second spring element may be permanently electrically connected to one of the contacts. For example, both spring elements are permanently abutting the PCBA at the respective contacts.

In more detail, the first spring element may be a metal pressing which comprises three free ends, from which free ends a first free end is permanently biased in abutment with the third contact, a second free end is held in the bridge in a position allowing abutment with the second arm if the second arm is elastically deflected a predefined degree towards the second free end the first arm, and a third free end is the free end constituting the first arm which is held in the bridge in a position allowing abutment with the first contact if the first free end is deflected a predefined distance towards the second free end upon axial movement of the chassis towards the ring during the first switch operation mode. As an example, the first spring element may have a generally V-shaped form with the first free end and the second free end forming the shanks of the V-shape. The third free end may branch off from the shank with the first free end such that the shank of the first arm together with the third free end has a Y-shape.

Further, the second spring element may be a metal pressing which comprises two free ends, from which free ends a first free end is permanently biased in abutment with the second contact, and the second free end forms the second arm which carries the actuator, e.g. a tooth-like protrusion of the second arm, wherein the actuator is guided on the ratchet profile at least during the second switch operation mode such that the second arm alternates between contacting bottom sections and peak sections of the ratchet profile thereby alternately elastically deflecting the second arm towards the first spring element. The second spring element may have a generally V-shaped form, too.

In this second example the bridge retaining the arms is arranged for example on top of the ring and may be held in an opening of the chassis permitting, e.g. limited, relative axial movement of the chassis and the PCBA with respect to the bridge and the ring. Thus, the switch assembly has the benefit of being highly reliable due to the arms being securely guided by the bridge with respect to the a ring and with respect to the chassis. The ring or a component part attached to the ring, like a dial sleeve or a dial sleeve assembly, may be provided with an, e.g. proximally facing, guiding surface for the bridge.

With this second example the number of additional component parts required to build the switch assembly is again relatively low. For example, in drug delivery devices with an electronic system comprising the ring, the chassis and the PCBA, it is only required to provide the bridge and the first and second arms which may be permanently retained in the bridge. Thus, it is only required to modify the chassis by providing an opening to receive the bridge to provide the switch assembly according to the present disclosure. With the above mentioned design of the second example, a fourth contact on the PCBA is not required for the function of the switch assembly. The low number of additional component parts contributes in making the assembly process highly efficient.

According to a third example, the first arm and the second arm may be free ends on a single, annular metal pressing which is preferably interposed between the chassis and the PCBA in a position permitting at least one elastically deformable contact tab of the pressing to abut the third contact of the PCBA. The annular metal pressing may further comprise a lever located such that the lever abuts a proximally facing annular guiding surface of the ring when a predefined axial movement of the chassis towards the ring occurs during the first switch operation mode, thereby deflecting the first arm to abut the first electrical contact. In addition, or as an alternative, the annular metal pressing may further comprise an actuator lever located such that the actuator lever abuts the proximally facing ratchet profile of the ring at least after the first switch operation mode. Preferably, the actuator lever is guided on the ratchet profile and alternates between contacting bottom sections and peak sections of the ratchet profile at least during the second switch operation mode such that the actuator lever alternately elastically deforms the second arm thereby opening and closing an electrical connection between the second electrical contact and the second arm.

In other words, the switch may be substantially formed by a metal pressing in the form of a slotted disc from which several arms are bent off. With this third example the number of additional component parts required to build the switch assembly is further reduced. For example, in drug delivery devices with an electronic system comprising the ring, the chassis and the PCBA, it is only required to provide the slotted disc which is interposed between the chassis and the PCBA. With the above mentioned design of the third example, a fourth contact on the PCBA is not required for the function of the switch assembly. The low number of additional component parts contributes in making the assembly process highly efficient.

According to a fourth example, the switch assembly may further comprise a first electrically conductive spring element and a bridge holding a second electrically conductive spring element. The bridge may be arranged in the chassis interposed between the ring and a biasing arm, e.g. of the first spring element, such that the bridge is held in abutment with the ring by the biasing arm and is axially displaceable relative to the chassis against the bias of the biasing arm upon axial movement of the chassis towards the ring during the first switch operation mode.

In more detail, the first arm may be part of the first electrically conductive spring element which further comprises a contact tab held in the chassis in a position permitting the contact tab to abut the third contact of the PCBA. Further, the bridge may be arranged in the chassis such that the bridge elastically deflects the first arm upon axial movement of the chassis towards the ring during the first switch operation mode thereby closing an electrical connection between the first electrical contact and the first arm. In addition, the second spring element may be a metal pressing which comprises two free ends, from which free ends a first free end is biased in abutment with the second contact at least during the second switch operation mode, and the second free end forms the second arm which carries the actuator, preferably a tooth-like protrusion of the second arm, wherein the actuator may be guided on the ratchet profile at least during the second switch operation mode such that the second arm alternates between contacting bottom sections and peak sections of the ratchet profile thereby alternately elastically deflecting the second arm towards the first spring element.

In this fourth example the first spring element may be directly interposed and held between the chassis and the PCBA, while the bridge retaining the the second spring element is arranged for example on top of the ring and may be held in an opening of the chassis permitting, e.g. limited, relative axial movement of the chassis and the PCBA with respect to the bridge and the ring. Thus, the switch assembly has the benefit of being highly reliable due to the spring elements being securely guided with respect to the a ring and with respect to the chassis. The ring or a component part attached to the ring, like a dial sleeve or a dial sleeve assembly, may be provided with an, e.g. proximally facing, guiding surface for the bridge.

With this fourth example the number of additional component parts required to build the switch assembly is again relatively low. For example, in drug delivery devices with an electronic system comprising the ring, the chassis and the PCBA, it is only required to provide the bridge and the first and second spring elements. Thus, it is only required to modify the chassis by providing an opening to receive the bridge to provide the switch assembly according to the present disclosure. With the above mentioned design of the second example, a fourth contact on the PCBA is not required for the function of the switch assembly. The low number of additional component parts contributes in making the assembly process highly efficient.

The examples of the switch assemblies are especially applicable in drug delivery devices comprising an electronic system. The present disclosure is applicable for devices which are manually driven, e.g. by a user applying a force to an injection button, for devices which are driven by a spring or the like and for devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

According to one aspect of the present disclosure, a drug delivery device may comprise an electronic system with the switch assembly as described above. For example, the drug delivery device may comprise a dose setting and drive mechanism and a button module. In more detail, the dose setting and drive mechanism may be configured to perform a dose setting operation for setting a dose to be delivered by the drug delivery device and a dose delivery operation for delivering the set dose. Preferably, the dose setting and drive mechanism comprises the ring of the switch assembly. Further, the button module may comprise an electronic control unit on the PCBA, a rotary sensor, e.g. with a light source and a corresponding optical sensor, a communication unit with a wireless communication interface for communicating with another device, and a use detection unit comprising the switch assembly. Preferably, the electronic control unit is configured to control an operation of the electronic system.

According to a further aspect of the present disclosure, the button module and the dose setting and drive mechanism may be configured such that the dose dial assembly rotates relative to the button module during the dose delivery operation but does not rotate relative to the button module during the dose setting operation and that the button module moves axially relative to the dose dial assembly during the transition from the dose setting operation to the dose delivery operation, or when the button module is pressed in a 0U dialed condition.

According to a further aspect of the present disclosure, the electronic system is configured such that the communication unit is switched from a sleeping mode into an operation mode inducing the communication unit to initiate a manual synchronisation and/or a pairing with another device upon closing an electrical connection between the first electrical contact and the first arm during the first switch operation mode. In addition or as an alternative, the electronic system is configured such that the rotary sensor is switched from a sleeping mode into an operation mode inducing the rotary sensor to initiate a motion detection upon closing an electrical connection between the second electrical contact and the third electrical contact via the second arm during the second switch operation mode.

The present disclosure provides advantageous embodiments relating to the integration of mechanically activated electronic switches to initiate different device functions. The at least one switch assembly may form or may be part of a use detection unit of the electronic system. Such a use detection unit may comprise the use of a rotationally activated electronic switch (rotational switch) to wake an electronic encoding module attached to an injection device and/or the use of an axially activated electronic switch (axial switch) to initiate pairing functionality of an encoding module, e.g. a rotary sensor, attached to an injection device, with another smart electronic device. A mechanically activated electronic switch may be or may form part of an electrical use detection unit operatively connected to an electronic control unit. The electrical use detection unit may be configured to generate a first signal which is indicative that the user has commenced or finished the relative movement between the dose setting and drive mechanism and the button module. Thus, the present disclosure permits an injection device to maintain a low power state when energising of the encoding sensor(s) or pairing is not required, but to wake when either functionality is required. This is especially applicable to devices where a module rotates relative to an axially adjacent mechanism component during dose delivery but does not rotate relative to that component during dialing and/or to devices where the module moves axially relative to an adjacent mechanism component during the transition from a dialling to a dispensing state, or when the button module is pressed in a 0U dialed condition, i.e. a state at the completion of dose dispensing and prior to selecting a new dose.

According to one aspect of the present disclosure an electronic system comprises a dose setting and drive mechanism which is configured to perform a dose setting operation for setting a dose to be delivered by the drug delivery device and a dose delivery operation for delivering the set dose. The dose setting and drive mechanism comprises at least a ring which may be, preferably indirectly, operable by a user during the dose setting operation and/or the dose delivery operation. For example, the dose setting and drive mechanism may comprise one or more of the following components: a dial grip, a dial or display member (e.g. a number sleeve), a driver, a clutch, a piston rod, an inner and/or outer housing component. The dose setting and drive mechanism of the present disclosure may be based on the dose setting and drive mechanism disclosed in EP 2 890 435.

According to a further aspect of the present disclosure an electronic system comprises a button module comprising at least an electronic control unit, e.g. consisting of or comprising a PCBA, being configured to control an operation of the electronic system. The button module may be permanently or detachably attached to a trigger, a button or a dial grip, e.g. at or near the proximal end of the drug delivery device. The button module and/or the electronic control unit may have a distal surface facing towards the dose setting and drive mechanism, for example for providing an interface for mechanical interaction and/or electrical connection with further component parts of the system.

In one embodiment, the electronic system has a first state and a second state. The first state and the second state may be different states of operation of the electronic system. The electronic control unit may have at least a first, preferably low power consumption, state and a second, preferably high power consumption, state. In the first state, the system may be in an idle state, where the system could not operate with the desired functionality assigned to the electronic system, e.g. use detection, motion detection, encoding, synchronisation and/or pairing. In other words, at least one function may be not activated in this first state. In the second state, the system may be ready to operate with the desired functionality, e.g. when the system is triggered to start an operation and/or when in the second state a dose setting operation and/or a dose delivery operation is being performed. The electronic system may have an increased electrical power consumption in the second state as compared to the first state. For example, in the second state, one or more electrical or electronic units of the electronic system may be switched to a state of higher power consumption, e.g. an on state, as compared to the first state, where the respective unit may be in a sleep state with low power consumption or an off state with no power consumption at all, e.g. because the connection to an electrical power supply is interrupted. For example, a communication unit and/or an encoding module. e.g. a rotary sensor, may be activated in this second state.

An encoding module or unit is typically suitable to detect a motion of a specific component part of the dose setting and drive mechanism and to generate signals indicative of the amount of motion of this component part. For example, the encoding module or unit may detect rotational movement of an encoder ring attached to a dial sleeve, which encoder ring is preferably the ring of the switch assembly, during the dose setting operation and/or during the dose delivery operation. According to one aspect of the present disclosure, the encoding module comprises a rotary sensor for detection of a rotational movement. A rotary sensor may comprise a light source with a corresponding optical sensor, preferably two light sources with two corresponding optical sensors, for detecting a rotational movement of a component part having a pattern. As an alternative, a rotary sensor may use other detection techniques, e.g. the rotary sensor may comprise an electrical sliding contact, a mechanical switching arrangement and/or a magnetic sensor.

For example, the encoder ring may further comprise a pattern provided at least on its outer surface which can be detected by the rotary sensor. According to one aspect, the rotary sensor comprises a primary sensor and secondary sensor which are configured to target specially adapted regions at the proximal end of the dial sleeve, e.g. at the encoder ring. In this example, the primary sensor and the secondary sensor may be light reflective sensors. Therefore, the specially adapted proximal regions of the dial sleeve or the encoder ring may be divided into at least one reflective area and at least one non-reflective (or absorbent) area. The rotary sensor may be an optical sensor emitting light from an LED whose light is reflected by the reflective region(s) of the encoder ring and the sensor detects the reflected light. The sensor then converts the detected light to an electrical output. The encoding or motion sensing unit may comprise one or more of such optical rotary sensor(s), for example two optical rotary sensors located circumferentially spaced about the encoder ring.

The electronic system may further comprise an encoding or motion sensing unit which is in a sleeping mode in the first low power consumption state and which is activated in the second high power consumption state, and/or a communication unit for communicating with another device, which communication unit is in a sleeping mode in the first low power consumption state and which is activated in the second high power consumption state. In an exemplary embodiment of the present disclosure, the electronic system may comprise an encoding or motion sensing unit and a communication unit wherein both units may be independently activated or in a sleeping mode. Thus, there may be more than two power consumption states, namely a state where both units are deactivated or in a sleeping mode, a state where only the encoding or motion sensing unit is activated, a state where only the communication unit is activated and a state where both units are activated. The power consumption of the electronic system may be different for each of these four states. Nevertheless, only a first low power consumption state and a second high power consumption state are discussed herein for simplification reasons.

In an embodiment, the electronic system may be suitable to collect or measure dose data, e.g. corresponding to the set dose or the dispensed dose, using the encoding or motion sensing unit. Such dose data may be collected only in the second state of the system. In one embodiment, the encoding or motion sensing unit, when it is active, may be operable to gather motion data or measurement data relating to the movement of e.g. a dial member, a driver and/or a piston rod. The electronic control unit may be configured to convert this data into dose data, e.g. characteristic for the size of the dose which has been set or has been delivered in the respective operation. The encoding or motion sensing unit may be designed as described in unpublished EP20315066.9 and EP20315357.2, the disclosure of which is incorporated herein by reference.

The communication unit may comprise a wireless communication interface for communicating with another device, wherein the electronic system is configured such that it is switched from the first state into the second state by the electronic control unit in response to the first signal, thereby inducing the communication unit to initiate a manual synchronisation and/or a pairing with another device.

The electronic control unit may, in response to reception of the first signal issue a command, e.g. a signal, to another unit of the electronic system such that this unit is switched on or rendered operational. This unit may be the communication unit for communicating with another device, e.g. a wireless communications interface for communicating with another device via a wireless network such as Wi-Fi or Bluetooth®, or even an interface for a wired communications link, such as a socket for receiving a Universal Series Bus (USB), mini-USB or micro-USB connector. Preferably, the electronic system comprises an RF, WiFi and/or Bluetooth unit as the communication unit. The communication unit may be provided as a communication interface between the system or the drug delivery device and the exterior, such as other electronic devices, e.g. mobile phones, personal computers, laptops and so on. For example, dose data may be transmitted by the communication unit to the external device. The dose data may be used for a dose log or dose history established in the external device.

In one embodiment, the communication unit comprises a wireless communication interface for communicating with another device, wherein the electronic system is configured such that it is switched from the first state into the second state by the electronic control unit in response to the first signal of the at least one switch of the use detection unit, thereby inducing the communication unit to initiate a manual synchronisation and/or a pairing with another device or to initiate a mode for amending the settings of the electronic system.

According to one aspect of the present disclosure an electronic system comprises a dose setting and drive mechanism, an electrical power supply, e.g. a rechargeable or non-rechargeable battery, an electronic control unit, an electrical use detection unit and an encoding or motion sensing unit and/or a communication unit for communicating with another device.

In one embodiment, the device or the electronic system comprises an electronic control unit, e.g. comprising a microprocessor or microcontroller. The electronic control unit may be configured to control operation of the drug delivery device or the electronic system. The electronic control unit may be arranged on a conductor carrier and electrically conductively connected with conductors on the conductor carrier. The conductor carrier may be a circuit board such as a printed circuit board. The conductor carrier may be retained in the interior of the user interface member of the system or the device. The power supply may be arranged in the interior of the electronic system such as in the interior of the user interface member.

According to one aspect of the present disclosure, the electronic system is applicable to limit the battery capacity requirement of an injection device, where it is advantageous to be able to have the device in a low power state when any electronic functionality is not required. This can be achieved by mechanical switches which are activated by relative motion between the electronic button module and adjacent components as required, e.g. the above exemplarily mentioned encoder ring as part of the dial sleeve assembly.

According to one aspect of the present disclosure, the functionality of a manual synchronization is to be initiated on pressing the button module, when the device is at 0U dialed. When the button module is pressed, in any device state, the button module is translated, e.g. together with a clutch, distally relative to the dial sleeve assembly. The nominal axial travel may be limited, e.g. to less than 3 mm, for example to between 1.5 mm and 2.0 mm, travel of the button module relative to the dial sleeve (and the encoder ring), further relative axial motion is limited. The axial switch of one embodiment of the use detection unit is mounted in the underside of the button module and utilises the relative axial displacement between button module and dial sleeve assembly to trigger. The duration for which the button module is held in a depressed state may be used to allow multiple different functionalities to be initiated by the same switch, e.g. manual synchronisation for a short duration press and release, or pairing for a longer duration press and release.

According to one further aspect of the present disclosure, the functionality of e.g. encoding may be required to be initiated only when the device is dispensing. For example, in the device disclosed in EP 2 890 435, during dose setting the dial sleeve assembly, e.g. consisting of a dial sleeve and the encoder ring, and the button module extend (translate) helically from the device. Therefore there is no relative rotation between the button module and the dial sleeve assembly during dose setting. To initiate dose delivery the button module, e.g. and a clutch, are translated distally relative to the device housing. After the clutch has translated a predefined distance, e.g. less than 2.0 mm, for example nominally 1.20 mm, the clutch disengages from the dial sleeve and the delivery mechanism enters the dispensing (dose delivery) mode. In this dispensing mode the dial sleeve assembly retracts along the helical path into the device, whereas the button module does not rotate and only retracts with axial motion, until the 0U stop is engaged and dispense is complete. Thereby there is relative rotation of the button module with respect to the dial sleeve assembly during dispense. In the exemplary embodiment of a rotational switch of the use detection unit, this rotational switch may be mounted in the underside of the button module and utilises the relative rotation between the button module and dial sleeve assembly to trigger.

In this exemplary application to the device disclosed in EP 2 890 435, the axial switch will also be triggered when the button module is pressed as part of a dispensing event. However, with the embodiment described the relative order of the rotational and axial switch state changes cannot be guaranteed. It is possible that the axial switch will not be triggered before the point of clutch disengagement, e.g. 1.2 mm button module translation, so some rotation of the dial sleeve assembly could occur prior to the axial switch state change. Use of the rotational switch to initiate e.g. an optical encoding system ensures that the delivered dose is accurately recorded, irrespective of the axial position of the button module. Without the requirement to trigger prior to clutch disengagement, the maximum deflection of the axial switch contacts and therefore the forces, stresses and package space of this axial switch can be minimised.

According to a further aspect of the present disclosure, the use detection unit comprises the axial switch and the rotational switch wherein the electronic control unit is adapted to switch the encoding or motion sensing unit into its low power consumption state in response to a signal that the axial switch is switched from its first electrical state, e.g. an electrically open circuit, into its second electrical state, e.g. an electrically closed circuit. In more detail, when the user releases the button module at the end of dispense (or midway through a dispense event) the button module and clutch translate proximally relative to the device, e.g. under a clutch spring force. The axial switch state will change during this motion but the rotational switch state will not. The change of state of the axial switch following a dispense event, provides information to the controller (electronic control unit) that the user has released the button module. Without this information, an increased delay period would be required prior to a readout of the dispensed dose being displayed, since the system must wait to check for no further rotational switch signals to determine if the dose is complete. This would have a negative implication on battery life and user experience. Thus, although the use detection unit may comprise only the axial switch or only the rotational switch, a combination of the axial switch and the rotational switch provides additional benefits exceeding the possibility of triggering two different functions with two different switches.

The present disclosure further pertains to a drug delivery device comprising the electronic system as described above. The drug delivery device may comprise a container receptacle which is releasably attached to the dose setting and drive mechanism. As an alternative, the container receptacle may be permanently attached to the dose setting and drive mechanism. The container receptacle is adapted to receive a container, e.g. a cartridge, containing a medicament.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders.

Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The terms “axial”, “radial”, or “circumferential” as used herein may be used with respect to a main longitudinal axis of the device, the cartridge, the housing or the cartridge holder, e.g. the axis which extends through the proximal and distal ends of the cartridge, the cartridge holder or the drug delivery device.

BRIEF DESCRIPTION OF THE FIGURES

Non-limiting, exemplary embodiments of the disclosure will now be described with reference to the accompanying drawings, in which.

In the figures, identical elements, identically acting elements or elements of the same kind may be provided with the same reference numerals.

DETAILED DESCRIPTION

Figure 1:
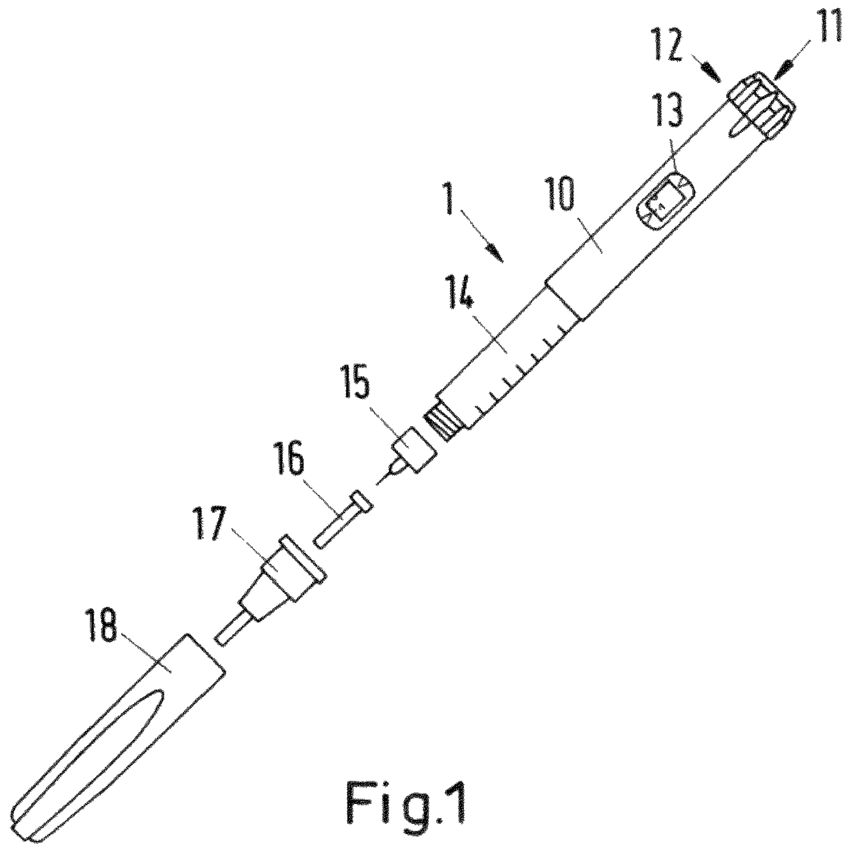
FIG. 1 shows an embodiment of a drug delivery device.

In the following, some embodiments will be described with reference to an insulin injection device. The present disclosure is however not limited to such application and may equally well be deployed with injection devices that are configured to eject other medicaments or drug delivery devices in general, preferably pen-type devices and/or injection devices.

Embodiments are provided in relation to injection devices, in particular to variable dose injection devices, which record and/or track data on doses delivered thereby. These data may include the size of the selected dose and/or the size of the actually delivered dose, the time and date of administration, the duration of the administration and the like. Features described herein include the arrangement of sensing elements and power management techniques (e.g. to facilitate small batteries and/or to enable efficient power usage).

Certain embodiments in this document are illustrated with respect to the injection device disclosed in EP 2 890 435 where an injection button and grip (dose setting member or dose setter) are combined. The injection button may provide the user interface member for initiating and/or performing a dose delivery operation of the drug delivery device. The grip or knob may provide the user interface member for initiating and/or performing a dose setting operation. These devices are of the dial extension type, i.e. their length increases during dose setting. Other injection devices with the same kinematical behaviour of the dial extension and button during dose setting and dose expelling operational mode are known as, for example, the Kwikpen® device marketed by Eli Lilly and the Novopen® 4 device marketed by Novo Nordisk. An application of the general principles to these devices therefore appears straightforward and further explanations will be omitted. However, the general principles of the present disclosure are not limited to that kinematical behaviour. Certain other embodiments may be conceived for application to Sanofi's SoloSTAR® injection device where there are separate injection button and grip components/dose setting members. Thus, there may be two separate user interface members, one for the dose setting operation and one for the dose delivery operation.

"Distal" is used herein to specify directions, ends or surfaces which are arranged or are to be arranged to face or point towards a dispensing end of the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example.

FIG. 1 is an exploded view of a medicament delivery device or drug delivery device. In this example, the medicament delivery device is an injection device 1, e.g. a pen-type injector, such an injection pen disclosed in EP 2 890 435.

The injection device 1 of FIG. 1 is an injection pen that comprises a housing 10 and contains a container 14, e.g. an insulin container, or a receptacle for such a container. The container may contain a drug. A needle 15 can be affixed to the container or the receptacle. The container may be a cartridge and the receptacle may be a cartridge holder. The needle is protected by an inner needle cap 16 and either an outer needle cap 17 or another cap 18. An insulin dose to be ejected from injection device 1 can be set, programmed, or 'dialed in' by turning a dosage knob 12, and a currently programmed or set dose is then displayed via dosage window 13, for instance in multiples of units. The indicia displayed in the window may be provided on a number sleeve or dial sleeve. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a dial sleeve assembly that is configured to move when the dial grip 12 is turned, to provide a visual indication of a currently set dose. The dial grip 12 is rotated on a helical path with respect to the housing 10 when setting a dose.

In this example, the dial grip 12 includes one or more formations to facilitate attachment of a data collection device. Especially, the dial grip 12 may be arranged to attach a button module 11 onto the dial grip 12. As an alternative, the dial grip may comprise such a button module of an electronic system.

The injection device 1 may be configured so that turning the dial grip 12 causes a mechanical click sound to provide acoustic feedback to a user. In this embodiment, the dial grip 12 also acts as an injection button. When needle 15 is stuck into a skin portion of a patient, and then dial grip 12 and/or the attached button module 11 is pushed in an axial direction, the insulin dose displayed in display window 13 will be ejected from injection device 1. When the needle 15 of injection device 1 remains for a certain time in the skin portion after the dial grip 12 is pushed, the dose is injected into the patient's body. Ejection of the insulin dose may also cause a mechanical click sound, which may be different from the sounds produced when rotating the dial grip 12 during dialing of the dose.

In this embodiment, during delivery of the insulin dose, the dial grip 12 is returned to its initial position in an axial movement, without rotation, while the dial sleeve assembly is rotated to return to its initial position, e.g. to display a dose of zero units. FIG. 1 shows the injection device 1 in this 0U dialed condition. As noted already, the disclosure is not restricted to insulin but should encompass all drugs in the drug container 14, especially liquid drugs or drug formulations.

Injection device 1 may be used for several injection processes until either the insulin container 14 is empty or the expiration date of the medicament in the injection device 1 (e.g. 28 days after the first use) is reached. In the case of a reusable device, it is possible to replace the insulin container.

Furthermore, before using injection device 1 for the first time, it may be necessary to perform a so-called "prime shot" to remove air from insulin container 14 and needle 15, for instance by selecting two units of insulin and pressing dial grip 12 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

As explained above, the dial grip 12 also functions as an injection button so that the same component is used for dialling/setting the dose and dispensing/delivering the dose. As an alternative (not shown), a separate injection button may be used which is axially displaceable, at least a limited distance, relative to the dial grip 12 to effect or trigger dose dispensing.

Figure 6:
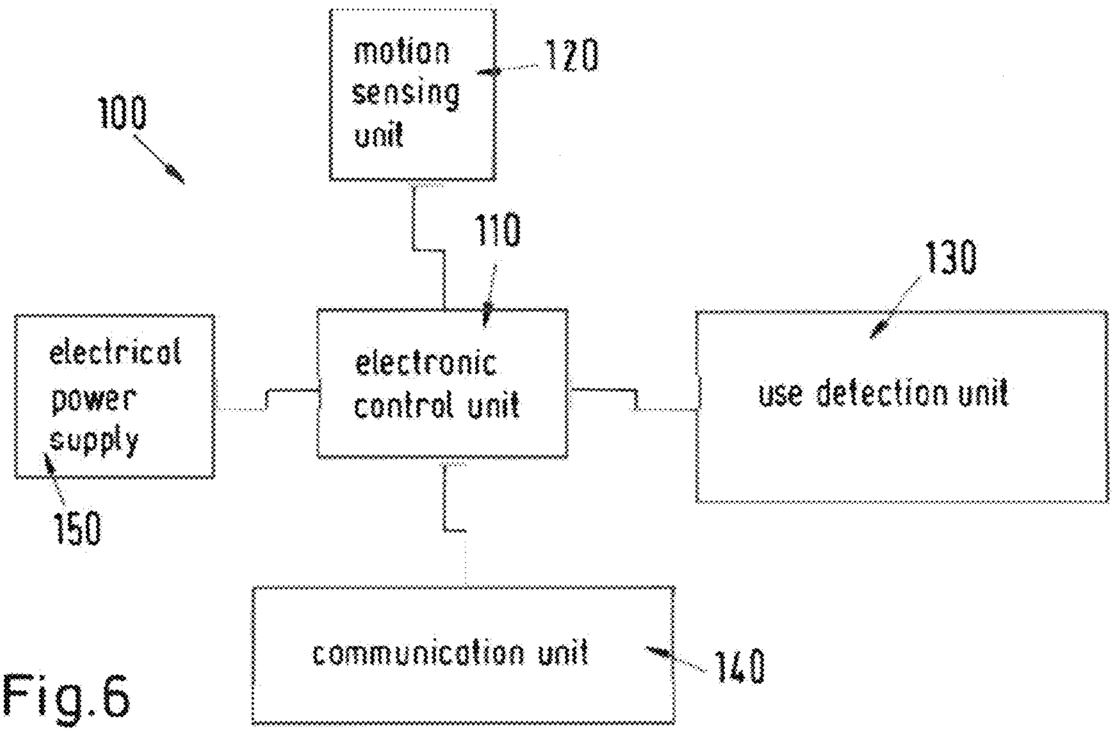
FIG. 6 illustrates schematically an embodiment of an electronic system for a drug delivery device.

In the following, an electronic system 100 according to the disclosure will be described with respect to exemplary embodiments and with reference to FIG. 6. The electronic system 100 comprises a dose setting and drive mechanism which may be part of an injection device 1 as depicted in FIG. 1 and an electrical power supply 150, e.g. a rechargeable or non-rechargeable battery, as shown in FIG. 6. The electronic system 100 further comprises an electronic control unit 110, e.g. comprising or consisting or being part of a PCBA, configured to control an operation of the electronic system 100 which has a first state and a second state, wherein the electronic system 100 has an increased electrical power consumption in the second state as compared to the first state. The electronic system 100 further comprises an encoding and motion sensing unit 120, e.g. a rotary sensor, and an electrical use detector unit 130 which is operatively connected to the electronic control unit 110 and which is configured to generate at least a first signal which is indicative that the user performs an operation. An example of such an operation is that the user of the injection device and/or the electronic system enters a manual synchronization or pairing mode of the electronic system 100 and/or that a user starts dose dispensing. The electronic system 100 is configured such that it is switched from the first state into the second state by the electronic control unit 110 in response to said first signal. The electronic system further comprises a communication unit 140 for communicating with another device. When the communication unit 140 is active to perform the manual synchronization or pairing mode, the electronic system 100 is in its second state. The PCBA of the electronic control unit 110 may be arranged on and/or in a module chassis 19 of the button module 11 (see FIGS. 2*b*, 3*b*, 4*c* and 5*a*).

Although not explicitly depicted, the electronic system 100 may comprise a, preferably permanent and/or non-volatile, storage or memory unit, which may store data related to the operation of the drug delivery device such as dose history data, for example.

Unless specifically disclosed otherwise in the following, the electronic system 100 may have the functions and may be arranged and/or designed as described in unpublished EP20315066.9 and EP20315357.2, the disclosure of which is incorporated herein by reference.

A first embodiment of a switch assembly 20 is depicted in FIGS. 2*a* to 2*d*.

Figure 2A:
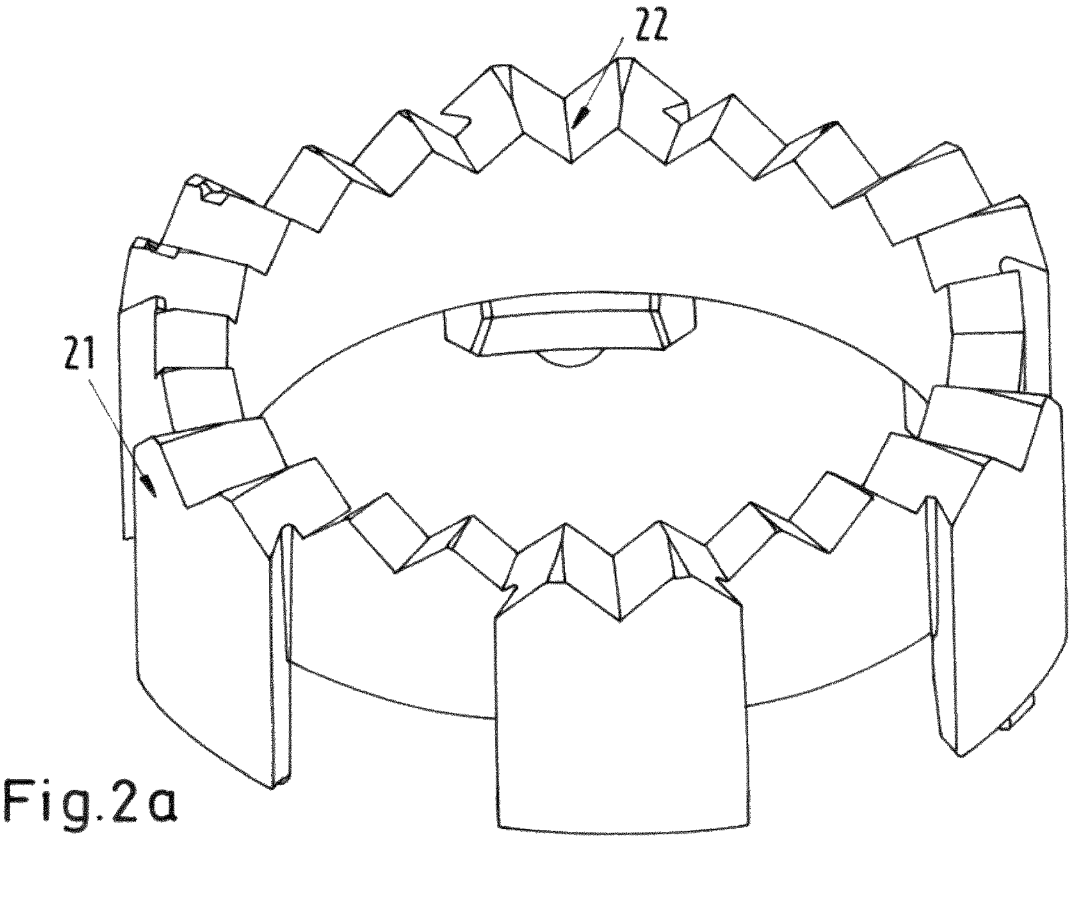
FIG. 2*a* shows a perspective view of a ring of the switch assembly according to a first embodiment of the present disclosure.

In the switch assembly 20, the button module 11 is arranged within the dial grip 12 and comprises the module chassis 19 on which the PCBA of the electronic control unit 110 is located. The module chassis 19 has an outer annual a portion held in the dial grip 12 and an inner tubular portion extending into an encoder ring 21 of a dial sleeve assembly. In the depicted embodiment the encoder ring 21 is a separate component part as shown in FIG. 2*a* fixed on the proximal end of a dial sleeve. As an alternative, the encoder ring 21 may be an integral part of a dial sleeve.

The encoder ring 21 comprises an annular ratchet profile 22 which is located facing proximally towards the distal surface of the PCBA of the electronic control unit 110. The distal surface of the PCBA of the electronic control unit 110 comprises a first electrical contact 23*a*, a second electrical contact 23*b*, a third electrical contact 23*c* and a fourth electrical contact 23*d*.

The switch assembly 20 further comprises an actuator in the form of a lever 24 which has a first end 25 which is hinged to the module chassis 19. The lever 24 may be an integral part of the module chassis 19. The lever 24 further comprises an opposite second end 26 which is a free end movable relative to the first end 25. The lever 24 is located within the module chassis 19 such that the free second end 26 may be brought in contact with the ratchet profile 22 of the encoder ring 21. For this purpose, the free second end 26 comprises a tooth-like protrusion facing distally towards the proximally extending ratchet profile 22 and adapted to interact with the ratchet profile 22.

Figure 2B:
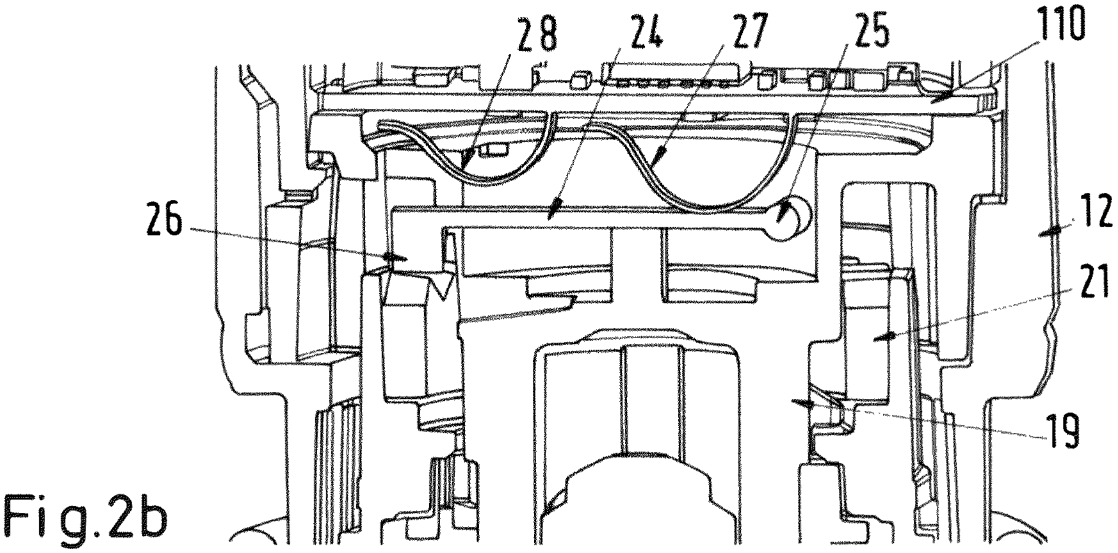
FIG. 2*b* shows a sectional view of the switch assembly according to the first embodiment in a default state.

Further, the switch assembly 20 comprises a first spring arm 27 and a second spring arm 28 which are both substantially U-shaped in the depicted embodiment. FIG. 2*b* shows both a spring arms 27, 28 and lever 24 in an unbiased default position, i.e. in a situation with no force applied to the lever and the spring arms. The first spring arm 27 is designed and arranged such that one of its ends, the right side end in the depicted embodiment, is permanently attached and in electrical connection with the fourth contact 23*d*, whereas the opposite end (left side in FIG. 2*b*) is located in the vicinity but spaced from the first contact 23*a*.

The first spring arm 27 thereby forms a switch between the first contact 23*a* and the fourth contact 23*d*. As will be explained below this first switch of the switch assembly 20 is operated by an axial movement of the chassis 19 with respect to the encoder ring 21. In a similar manner the second spring arm 28 is designed and arranged such that one of its ends, the right side end in the depicted embodiment, is permanently attached and in electrical connection with the third contact 23*c*, whereas the opposite end (left side in FIG. 2*b*) is located in the vicinity but spaced from the second contact 23*b*. The second spring arm 28 thereby forms a switch between the second contact 23*b* and the third contact 23*c*. As will be explained below this second switch of the switch assembly 20 is operated by a rotational movement of the encoder ring 21 with respect to the chassis 19.

In the embodiment depicted in the Figures, in the default position, the lever 24 is in abutment with a lower central portion of the first spring arm 27 at a position closer to the first end 25, whereas the lever 24 is spaced from a lower central portion of the second spring arm 28. As an alternative, the lever 24 may be spaced from the first spring arm 27 and the default position. The second spring arm 28 is arranged to abut the lever 24 upon deflection of the lever 24 at a position closer to the second end 26 of the lever 24.

In a default state of the drug delivery device, i.e. when the drug delivery device is not operated or manipulated by a user, the chassis 19, the ring 21, the lever 24 and the spring arms 27, 28 are arranged and in a state as depicted in FIG. 2*b*. In this a default state the axial switch and the rotational switch of the switch assembly 20 are both open, i.e. the first spring arm 27 is spaced from the first contact 23*a* and the second spring arm 28 is spaced from the second contact 23*b*.

During dose setting, i.e. when a user selects a higher or lower dose to be dispensed from the drug delivery device 1, the dial grip 12 is rotated by a user with respect to the housing 10. This causes the simultaneous rotation of the chassis 19 and the encoder ring 21 which are rotationally coupled to each other in the dose setting mode of the drug delivery device 1 via a clutch (not shown) of the dose setting and drive mechanism. Due to the simultaneous rotational movement of the chassis 19 and the encoder ring 21, the relative arrangement of the chassis 19, the ring 21, the lever 24 and the spring arms 27, 28 with respect to each other remains the same as in the default state depicted in FIG. 2*b*. During dose setting the dial grip 12 with the chassis 19 and the encoder ring 21 travel on a helical path thereby winding out of the housing 10 as of the selected dose is increased.

Figure 2C:
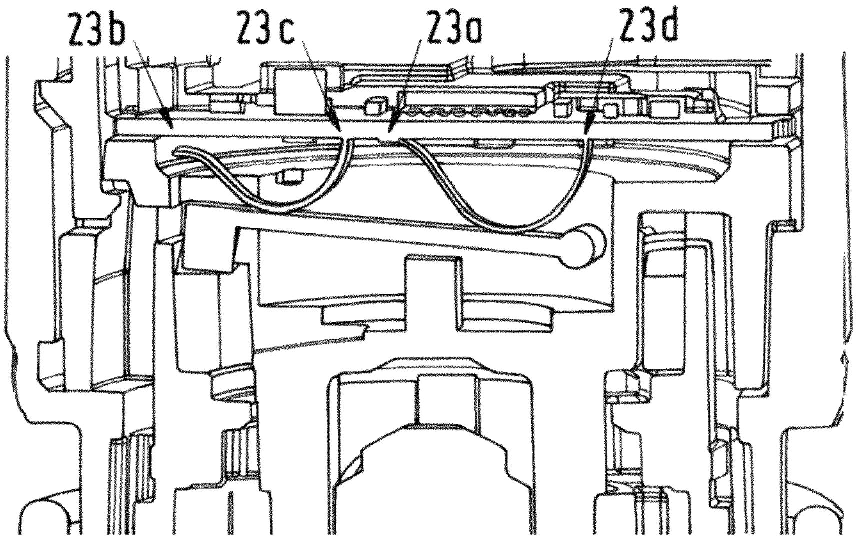
FIG. 2*c* shows a sectional view of the switch assembly according to the first embodiment in the first switch operation mode.

With the dose dialed, a user may start dose dispensing by axially pushing on the proximal end of the dial grip 12. This causes disengagement of the clutch to rotationally decouple the chassis 19 and the encoder ring 21 and causes rotationally coupling the dial grip 12 with the chassis 19 to the housing 10 of the drug delivery device 1. This axial movement includes a limited relative axial movement of the chassis 19 with respect to the encoder ring 21. FIG. 2*c* shows the switch assembly 20 after this limited relative axial movement. Due to this limited axial movement of the chassis 19 with respect to the encoder ring 21, the second free end 26 of the lever 24 engages a bottom section, i.e. a section between two peaks, of the ratchet profile 22 of the encoder ring 21 and is deflected proximally, i.e. upwards in FIG. 2*c*. this deflection of the lever 24 causes the first spring arm 27 to be deflected in the same direction, i.e. upwards, thereby closing the gap between the left end of the first spring arm 27 and the first contact 23*a*. In other words, the first axially operated switch of the switch assembly 20 is closed by this relative axial movement of the chassis 19 with respect to the encoder ring 21 due to actuation of the lever 24 which deflects the first spring arm 27. This constitutes a first switch operation mode of the switch assembly 20. The rotationally operated switch of the switch assembly 20 remains open as the gap between the second spring arm 28 and the second contact 23*b* is not closed.

Closing the axial switch of the switch assembly 20 may not only occur during this transition from the dose setting operation to the dose delivery operation of the drug delivery device 1 but may also occur when the dial grip 12, and thus the chassis 19, is pressed to move axially with respect to the encoder ring 21 in a 0U dialed condition of the drug delivery device 1, i.e. prior to dose setting.

This first switch operation mode is preferably used to wake up the communication unit 140, i.e. to switch the communication unit 140 from a sleeping mode into an operation mode inducing the communication unit 140 to initiate a manual synchronisation and/or a pairing with another device. This may occur by means of the electronic control unit 110 in response to the signal generated by closing the switch between the first spring arm 27 and the first contact 23*a*.

In other words, when the encoder ring 21 moves upwards as seen in the Figures relative to the chassis 19 where the lever 24 is attached, the free end 26 of the lever 24 is being pushed upwards. This causes the first spring arm 27 of the axial switch to come into contact with enclosing circuit on the PCBA. At this stage the lever 24 rests in a bottom section of the ratchet profile 22.

Figure 2D:
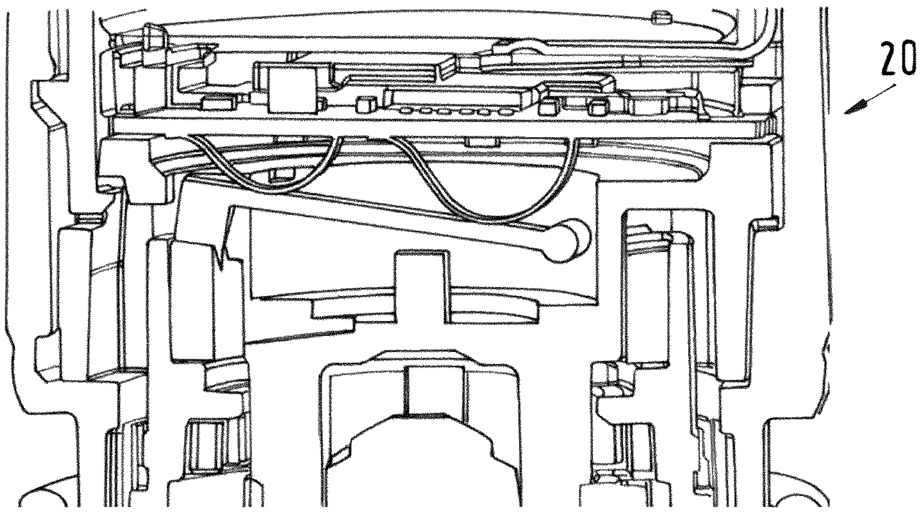
FIG. 2*d* shows a sectional view of the switch assembly according to the first embodiment in the second switch operation mode.

Further depression of the dial grip 12 causes of the dial grip 12 with the chassis 19 to be pushed axially back into the housing 10 while the encoder ring 21 rotates back into the housing 10 along the helical path. In other words, dose dispensing causes a relative rotational movement of the encoder ring 21 with respect to the chassis 19. During this rotational movement the tooth-like protrusion at the second free end 26 of the lever 24 slides over the ratchet profile 22 of the encoder ring 21. In other words, the second free end 26 of the lever 24 alternates between contacting bottom sections and peak sections of the ratchet profile 22 and thereby alternately deflects the lever 24 further. FIG. 2*d* shows the second free end 26 of the lever 24 contacting a peak section of the ratchet profile 22. This further deflection of the lever 24 causes the second spring arm 28 to be deflected, thereby closing the gap between the second spring arm 28 and the second contact 23*b*. This closes the rotational switch of the switch assembly 20. In other words, during this rotation the switch assembly 20 changes between the states depicted in FIG. 2*c* and the states depicted in FIG. 2*d*. This constitutes a second switch operation mode of the switch assembly 20.

The electronic system is preferably configured such that the rotary sensor 120 is switched from a sleeping mode into an operation mode inducing the rotary sensor 120 to initiate a motion detection upon closing the electrical connection between the second spring arm 28 and the second contact 23*b* during this second switch operation mode. This may occur by means of the electronic control unit 110 in response to the signal generated by closing the switch between the first second spring arm 28 and the second contact 23*b*.

In other words, when the encoder ring 21 starts to rotate the lever 24 will be pushed even further up, thereby engaging the second spring arm 28 of the rotational switch. This closes the circuit on the PCBA each time the free end 26 of the lever 24 passes over the peak of the ratchet profile 22. The axial switch remains engaged continuously throughout the rotational motion of the encoder ring 21.

The axial switch and the rotational switch of the switch assembly 20 both open as the user releases the dial grip 12 which causes the above described actions to be successively reversed.

A second embodiment of a switch assembly 30 is depicted in FIGS. 3*a* to 3*d*.

In the switch assembly 30, the arrangement of the button module 11, the dial grip 12 and the module chassis 19 with the PCBA of the electronic control unit 110 is as well as the arrangement of an encoder ring 31 is identical to the switch assembly 20. In addition, the relative movements of the module chassis 19 and the encoder ring 31 during the different operational stages of the drug delivery device 1 are identical. The encoder ring 31 comprises a ratchet profile as described above with respect to the switch assembly 20.

Figure 3A:
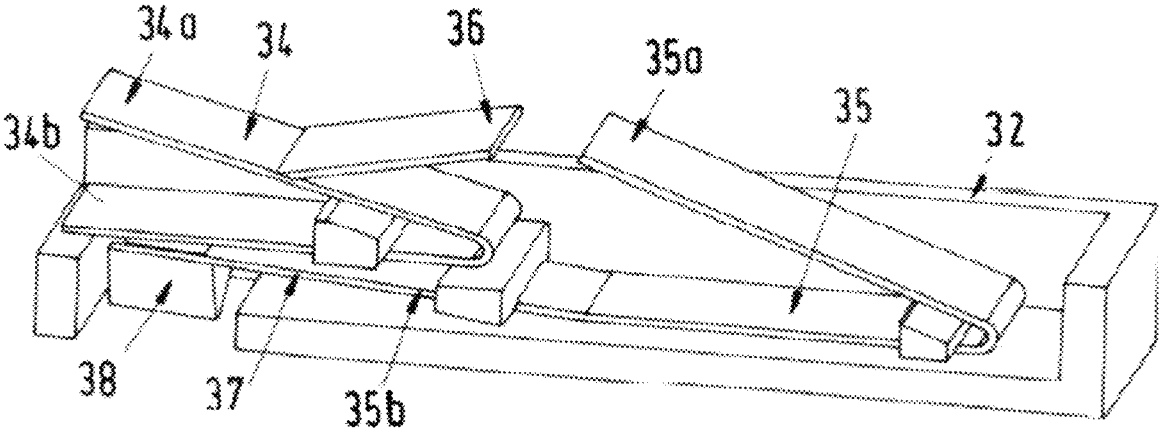
FIG. 3*a* shows a perspective view of a bridge of the switch assembly according to a second embodiment of the present disclosure.
Figure 3B:
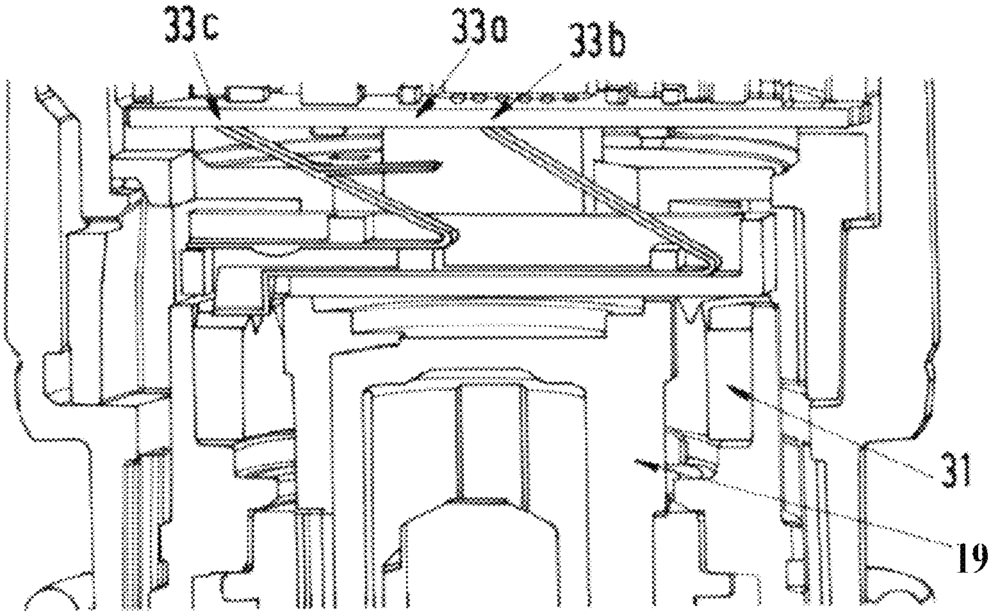
FIG. 3*b* shows a sectional view of the switch assembly according to the second embodiment in a default state.
Figure 3C:
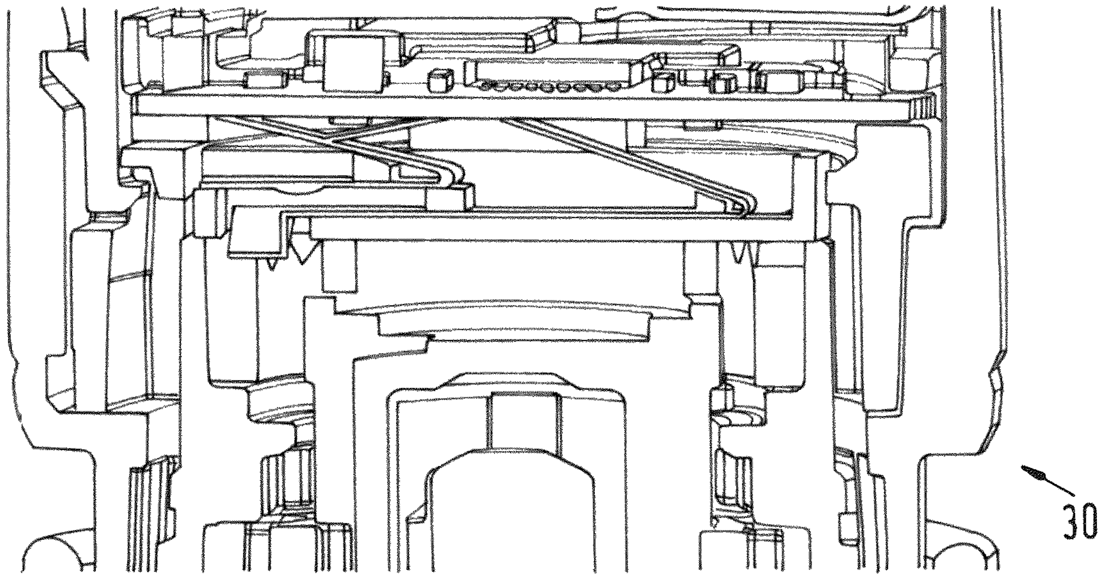
FIG. 3*c* shows a sectional view of the switch assembly according to the second embodiment in the first switch operation mode.
Figure 3D:
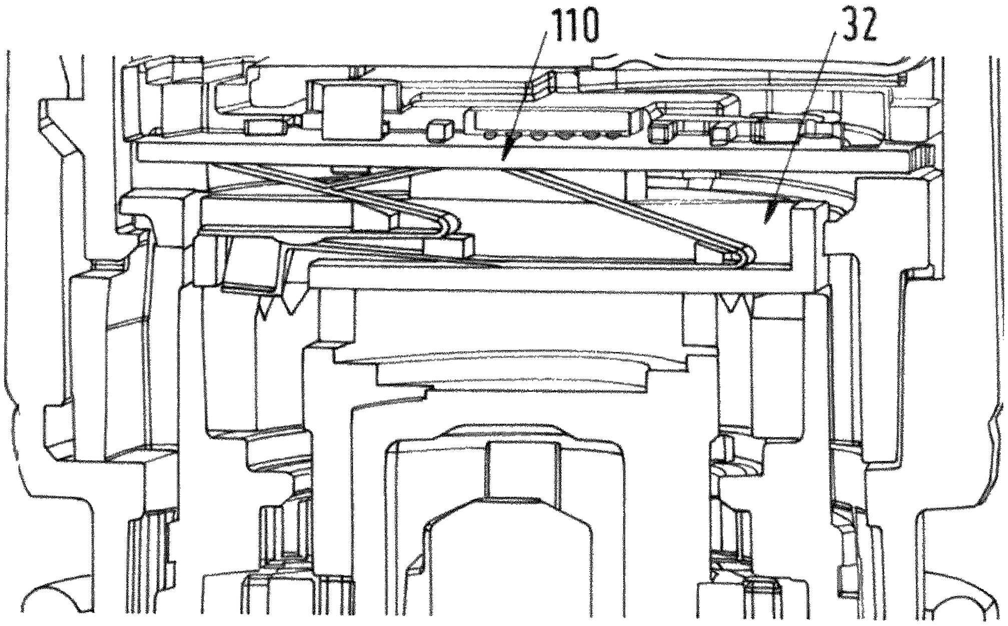
FIG. 3*d* shows a sectional view of the switch assembly according to the second embodiment in the second switch operation mode.

The switch assembly 30 comprises a bridge 32 shown in FIG. 3*a* which is interposed between the encoder ring 31 and the PCBA of the electronic control unit 110 partially extending through an opening in the chassis 19. The opening in the chassis 19 permits limited axial movement of the bridge 32 with respect to the chassis 19 as will be described below in more detail.

In the switch assembly 30, the distal surface of the PCBA of the electronic control unit 110 comprises a first electrical contact 33*a*, a second electrical contact 33*b* and a third electrical contact 33*c*. In addition, the switch assembly 30 comprises a first spring element 34 and a second spring element 35 which are both held by the bridge 32.

As shown in FIGS. 3*a* to 3*d*, the first spring element 34 substantially has a V-shaped form with a first free end 34*a* (upper end in the Figures) and a second free end 34*b* (lower end in the Figures) forming the shanks of the V-shape. A first spring arm 36 with a third free end branches off from the upper shank with the first end 34*a* such that the upper shank of the first arm 36 together substantially have a Y-shaped form. The second spring element 35 substantially has a V-shaped form with a first free end 35*a* (upper end in the Figures) and a second free end 35*b* (lower end in the Figures) forming the shanks or arms of the V-shape. The lower shank of the second spring element 35 is partially fixed in the bridge 32 with the second free end 35*b* forming a deflectable second arm 37 which has a distally facing tooth-like protrusion 38 at the second free end 35*b* which forms an actuator.

In the default state of the drug delivery device 1 and during dose setting, the first free end 34*a* of the first spring element 34 is biased against the third contact 33*c* and the first free end 35*a* of the second spring element 35 is biased against the second contact 33*b*, thereby pushing the bridge 32 in the distal direction (downwards in the Figures). The first arm 36 is spaced from the first contact 33*a*. Further, the second free end 34*b* of the first spring element 34 is spaced from the second arm 37 of the second spring element 35. In other words, neither the first contact 33*a* nor the second contact 33*b* is electrically connected to the third contact 33*c* via the first and second spring elements 34, 35.

If the user pushes the dial grip 12 either during the transition from dose setting to dose dispensing or in a in a 0U dialed condition of the drug delivery device 1, the relative axial movement of the chassis 19 with respect to the ring 31 results in a relative axial movement of chassis 19 with respect to the bridge 32. This deflects the upper shank of the first the spring element 34 such that the first arm 36 is brought in abutment with the first contact 33*a*. The gap between the second free end 34*b* of the first spring element 34 and the second arm 37 of the second spring element 35 remains open. This is the first switch operation mode of the switch assembly 30 which is preferably used to wake up the communication unit 140 as described above.

In other words, when the encoder ring 31 moves upwards as seen in the Figures relative to the chassis 19 where the bridge 32 is located, the bridge 32 is being pushed upwards. This causes the first arm 36 of the axial switch to come into contact with enclosing the circuit on the PCBA. At this stage the actuator 38 of the rotational switch rests in a bottom section of the ratchet profile.

During the dose delivery the encoder ring 31 rotates relative to the chassis 19 and the bridge 32. This causes the actuator, i.e. the distally facing tooth-like protrusion 38 to ride over the ratchet profile of the encoder ring 31. This alternately deflects the second arm 37 such that the gap between the second free end 34*b* of the first spring element 34 and the second arm 37 of the second spring element 35 is closed as the protrusion 38 rides over the peak of the ratchet profile and is opened again as of the protrusion 38 rides over a bottom section of the ratchet profile. This is the second switch operation mode of the switch assembly 30 which is preferably used to wake up the rotary sensor 120 as described above.

In other words, when the encoder ring 31 starts to rotate the actuator 38 of the rotational switch will be pushed up and come into contact with the first spring element 34 thereby closing a circuit on the PCBA each time the actuator 38 passes over a top of the ratchet profile. The axial switch remains engaged continuously throughout the rotational motion of the encoder ring 31.

A third embodiment of a switch assembly 40 is depicted in FIGS. 4*a* to 4*d*.

In the switch assembly 40, the arrangement of the button module 11, the dial grip 12 and the module chassis 19 with the PCBA of the electronic control unit 110 is as well as the arrangement of an encoder ring 41 is identical to the switch assemblies 20 and 30. The distal surface of the PCBA is provided with a first electrical contact, the second electrical contact and at least one third electrical contact in a similar manner as described above with respect to the switch assembly 30 (not shown in FIGS. 4*a* to 4*d*). In addition, the relative movements of the module chassis 19 and the encoder ring 41 during the different operational stages of the drug delivery device 1 are identical.

Figure 4A:
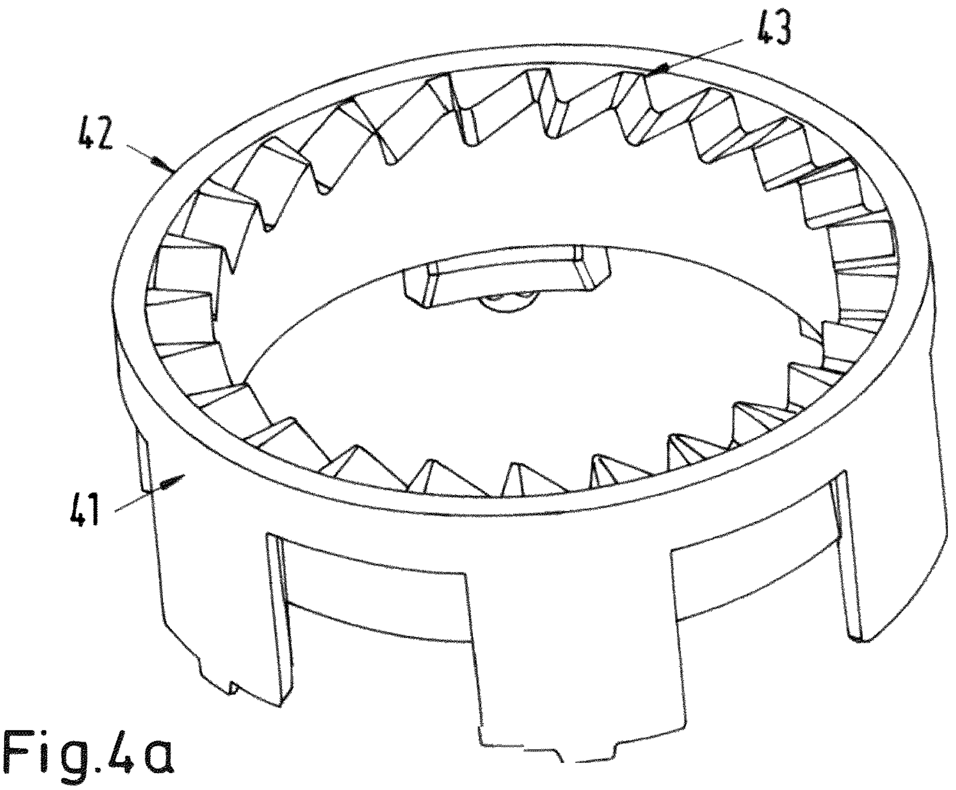
FIG. 4*a* shows a perspective view of a ring of the switch assembly according to a third embodiment of the present disclosure.

The encoder ring 41 comprises a ratchet profile 42 as described above with respect to the switch assembly 20. However, as depicted in FIG. 4*a*, the encoder ring 41 further comprises an annular guiding surface 43 surrounding the ratchet profile 42.

Figure 4B:
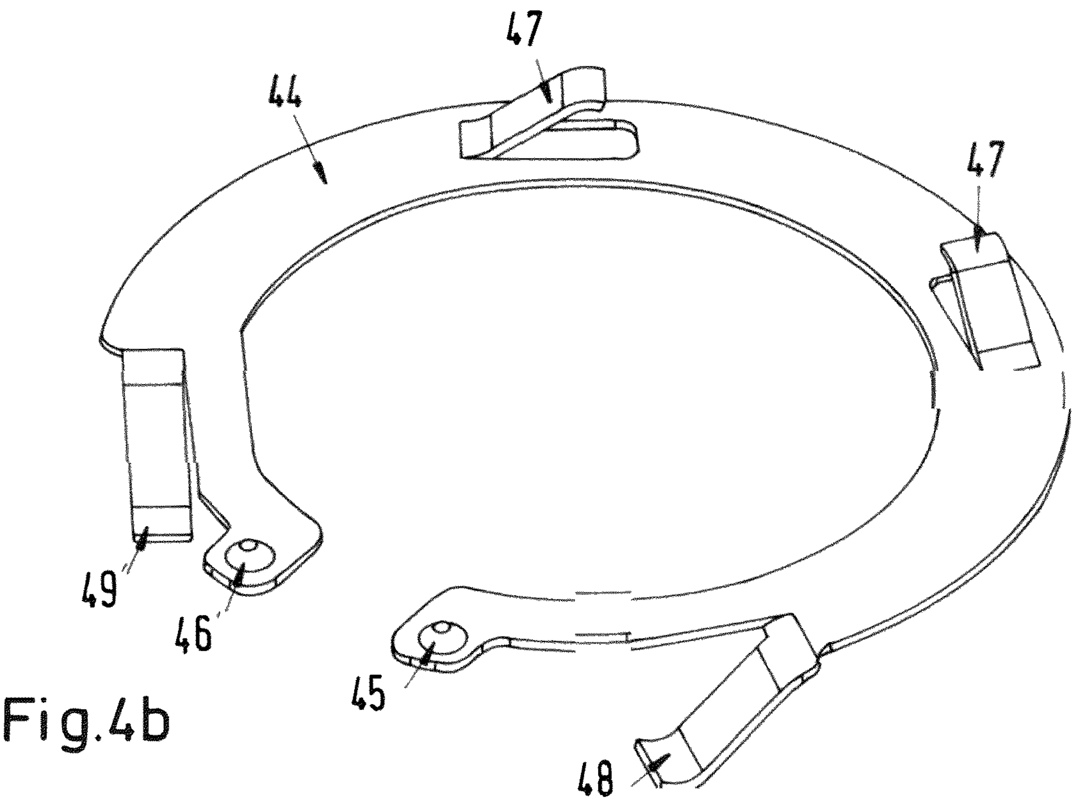
FIG. 4*b* shows a perspective view of a metal pressing of the switch assembly according to the third embodiment in a default state.
Figure 4C:
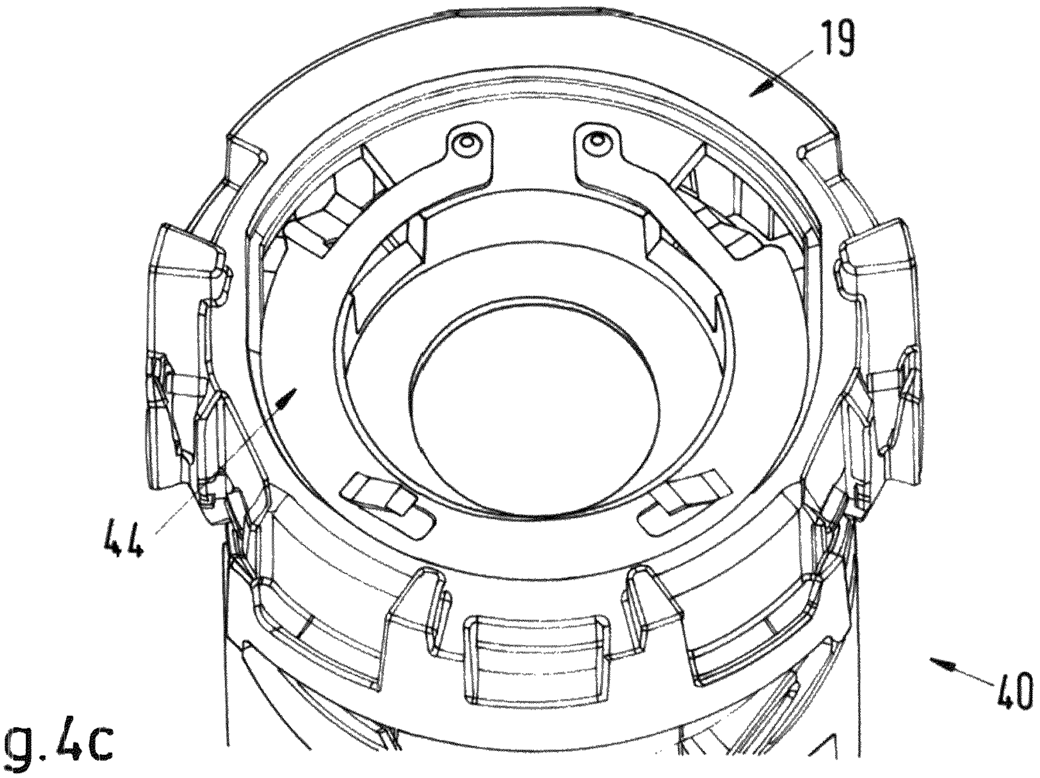
FIG. 4*c* shows a perspective view of the switch assembly according to the third embodiment in a default state.
Figure 4D:
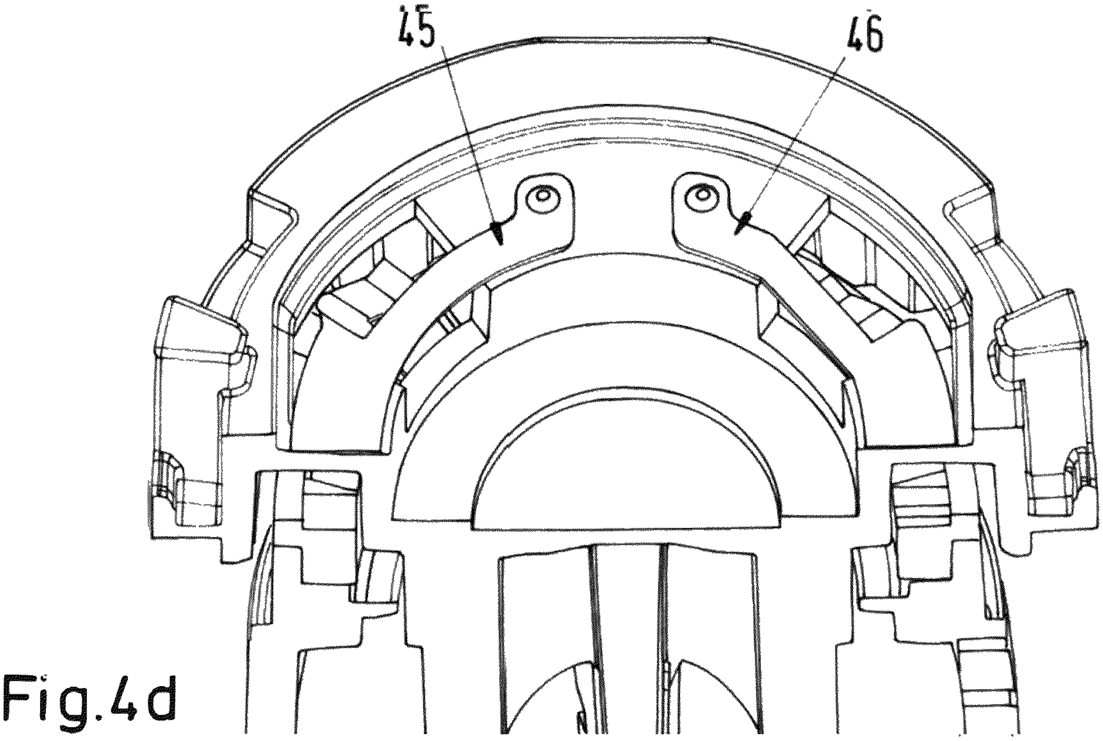
FIG. 4*d* shows a sectional view of the switch assembly of FIG. 4*c;*
Figure 5A:
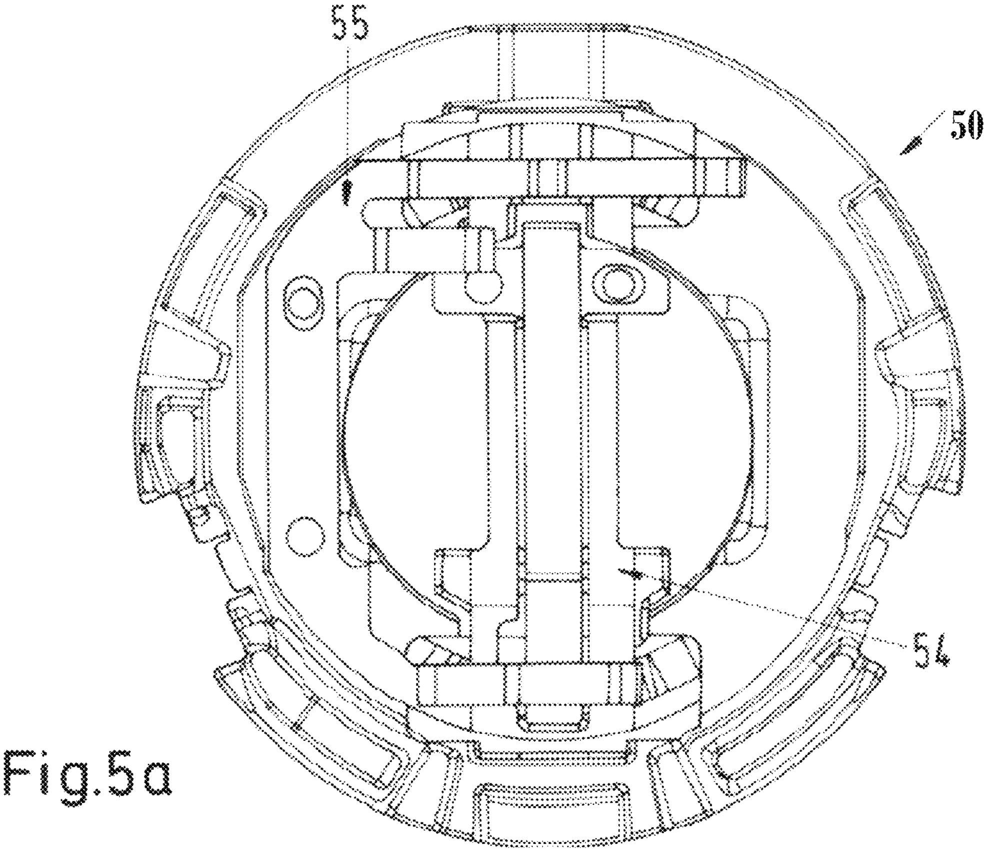
FIG. 5*a* shows a top view of the switch assembly according to a fourth embodiment of the present disclosure.
Figure 5B:
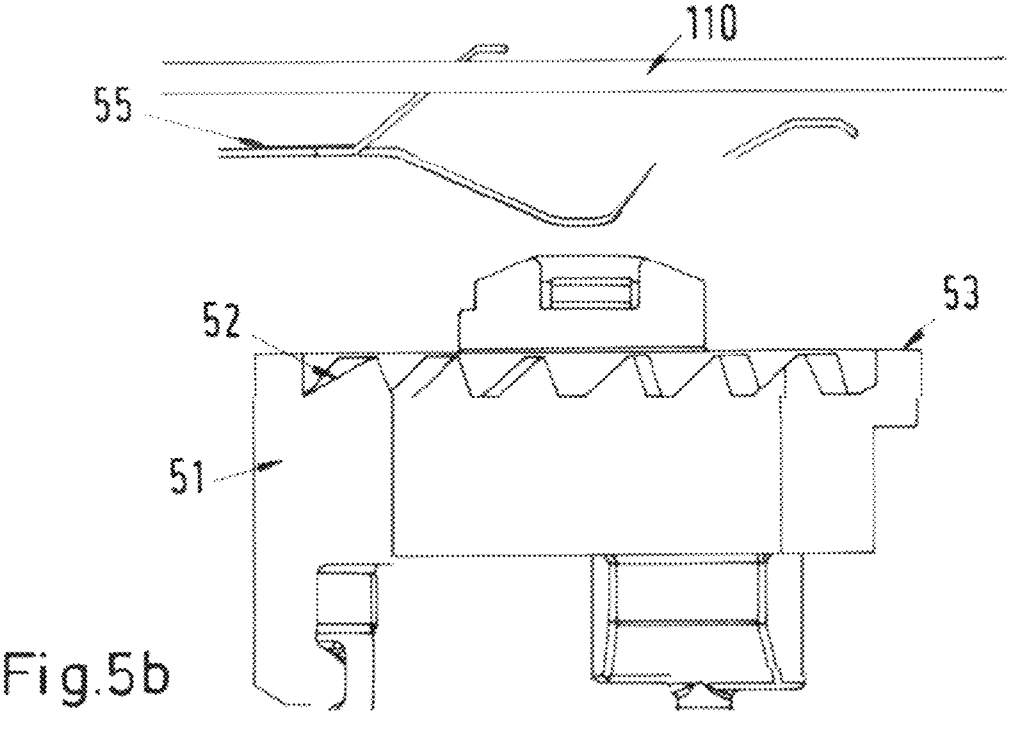
FIG. 5*b* shows a sectional view of the ring, the first spring element and the bridge of the switch assembly according to the fourth embodiment.
Figure 5C:
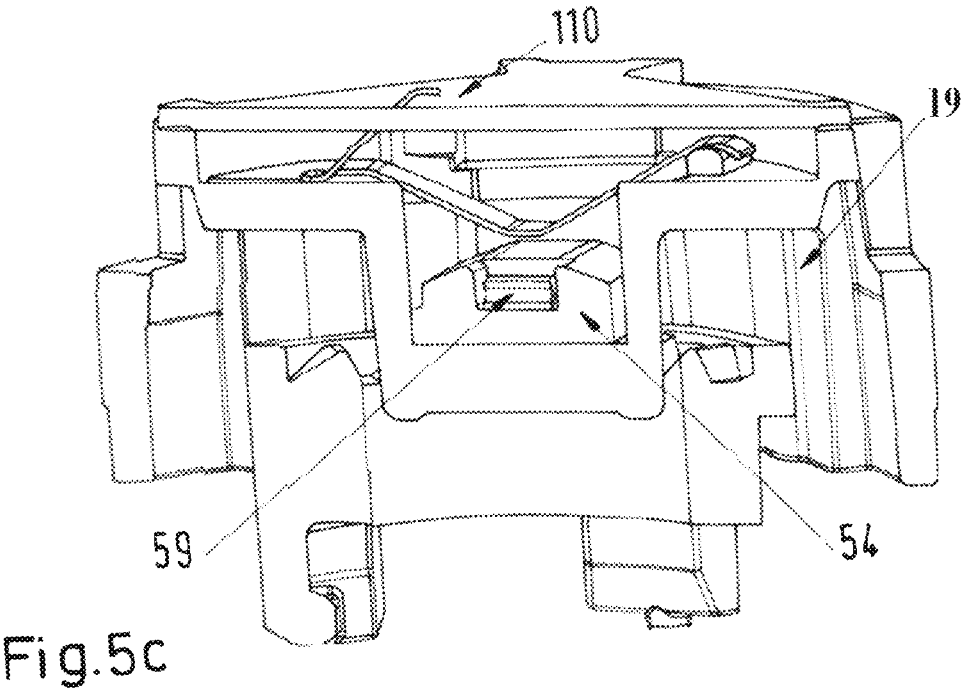
FIG. 5*c* shows a sectional view of the switch assembly according to the fourth embodiment.
Figure 5D:
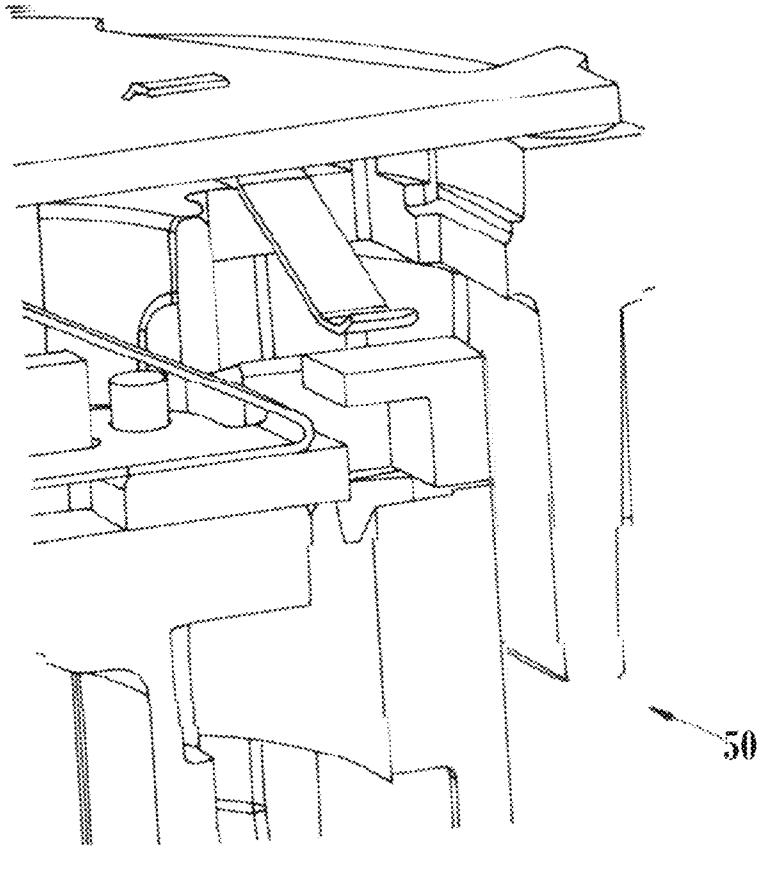
FIG. 5*d* shows a sectional view of a detail of the switch assembly according to the fourth embodiment.
Figure 5E:
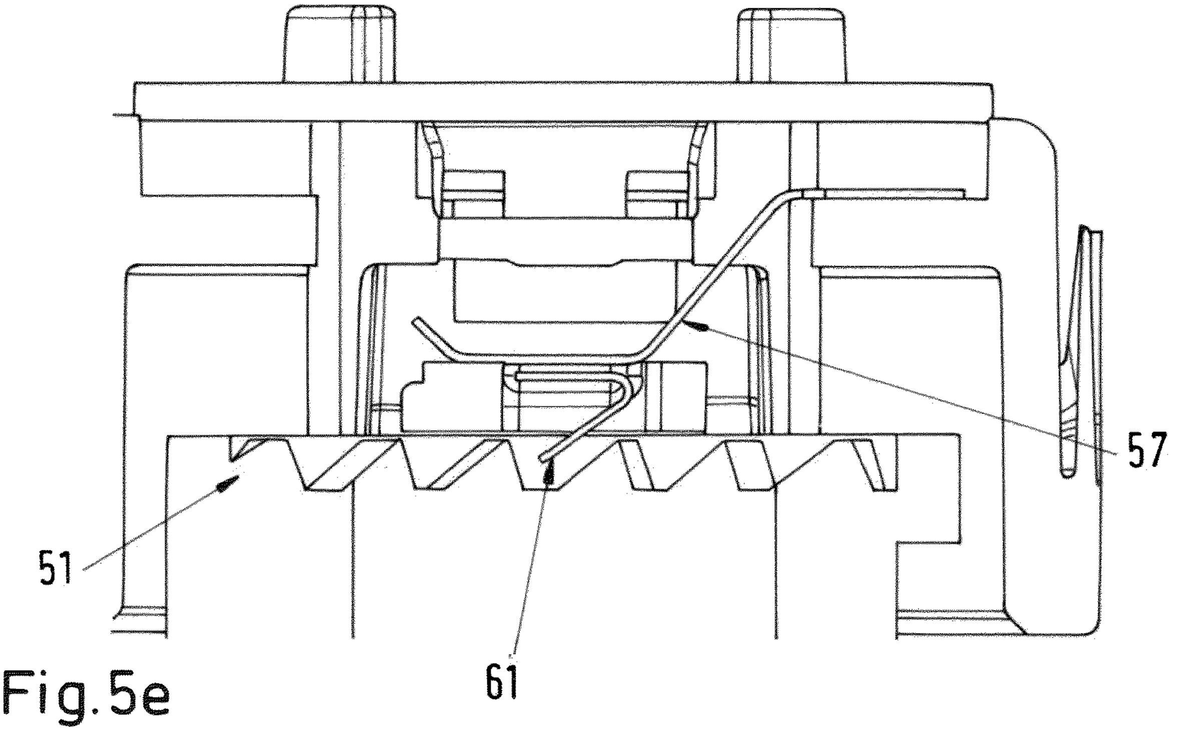
FIG. 5*e* shows a sectional view of a detail of the switch assembly according to the fourth embodiment.
Figure 5F:
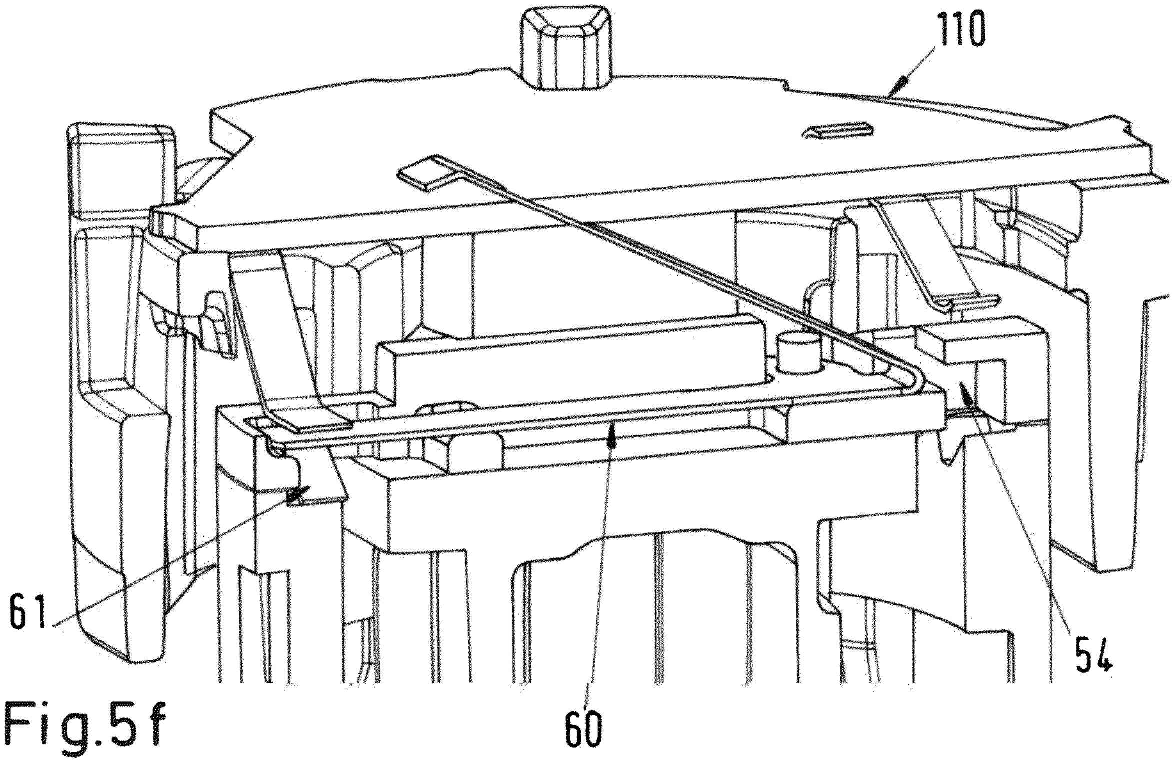
FIG. 5*f* shows a sectional view of a detail of the switch assembly according to the fourth embodiment.
Figure 5G:
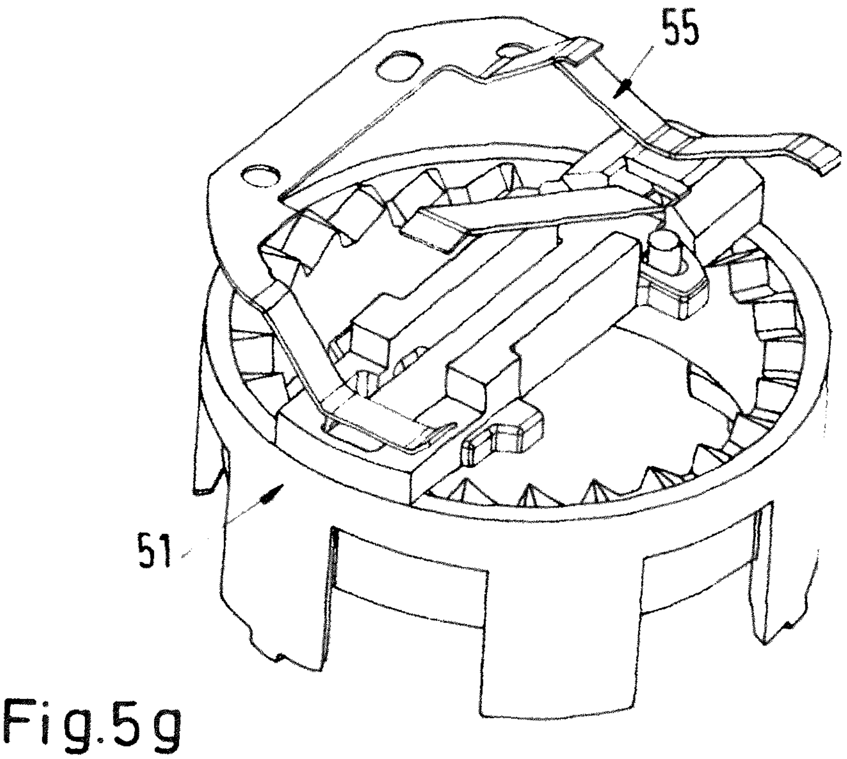
FIG. 5*g* shows a perspective view of a detail of the switch assembly according to the fourth embodiment.
Figure 5H:
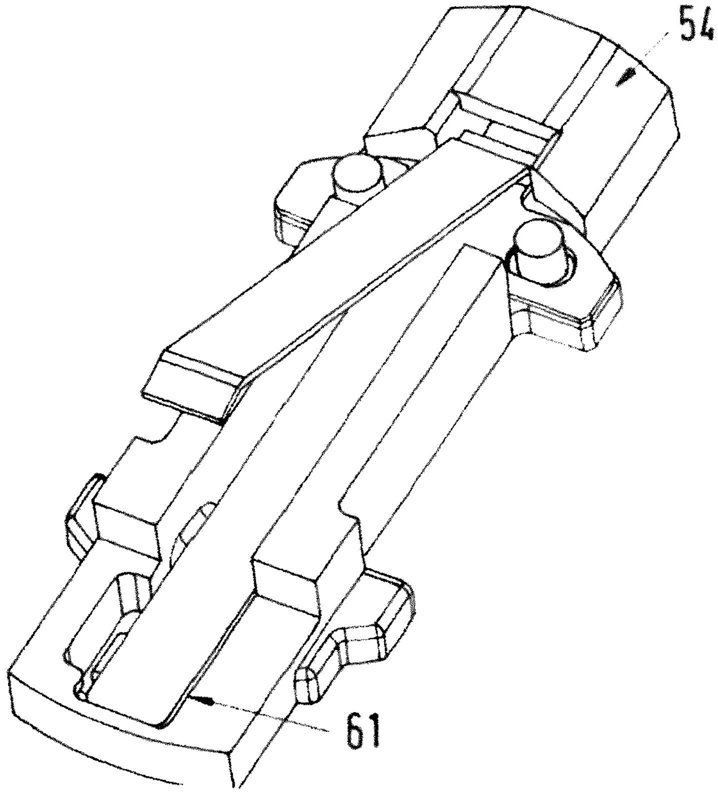
FIG. 5*h* shows a perspective view of the bridge of the switch assembly according to the fourth embodiment.
Figure 5I:
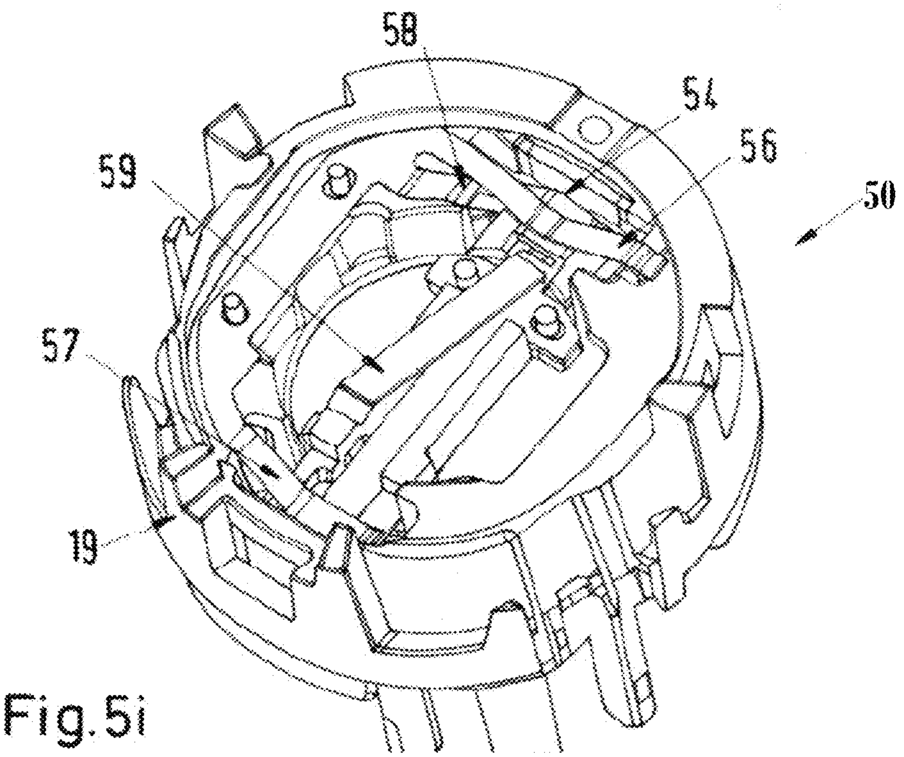
FIG. 5*i* shows a perspective view of the switch assembly according to the fourth embodiment.

The switch assembly 40 further comprises an annular metal pressing 44 in the form of a slotted disk. The metal pressing 44 comprises a first arm 45 and a second arm 46 which are arranged facing towards each other on either side of the slot. In addition, the metal pressing 44 comprises at least one contact tab 47 (two tabs 47 are depicted in FIGS. 4*b* to 4*d*). As can be best seen in FIG. 4*b*, a portion of the metal pressing 44 located radially outside of the first arm 45 is bent off from the plane of the slotted disk thereby forming a lever 48. In a similar manner an actuator lever 49 is provided by a portion of the metal pressing 44 located radially outside of the second arm 46. The lever 48 is located slightly further radially outwards compared with the actuator lever 49.

The annular metal pressing 44 is arranged on the chassis 19 interposed between the chassis 19 and the PCBA of the electronic control unit 110. The electrical contacts (not shown) on the distal surface of the PCBA are located such that the first electrical contact is arranged to be connected to the first arm 45, that the second electrical contact is arranged to be connected to the second arm 46 and that the at least one third electrical contact is arranged to be connected to the at least one tab 47. The lever 48 and to the actuator lever 49 extend through the respective openings in the chassis 19 such that the lever 48 is in contact with the annular guiding surface 43 while the actuator lever 49 is in contact with the ratchet profile 42.

In the default state of the drug delivery device 1, the first arm 45 is axially spaced from the first electrical contact and the second arm 46 is axially spaced from the second electrical contact, while the at least one contact tab 47 abuts the at least one third electrical contact of the PCBA. Thus, in the default state, neither the first electrical contact nor the second electrical contacts is connected to the third electrical contact via the annular metal pressing 44.

In the first switching mode of the switch assembly 40, i.e. when the dial grip 12 is depressed, the resulting axial movement of the chassis 19 relative to the encoder ring 41 results in the lever 48 being deflected in the proximal direction (upwards in the Figures) which in turn deflects the first arm 45 proximally to abut the first electrical contact on the PCBA. Closing the electrical connection between the first electrical contact and the third electrical contact via the deflected first arm 45 in the first switch operation mode of the switch assembly 40 is preferably used to wake up the communication unit 140 as described above.

In other words, when the encoder ring 41 moves upwards as seen in the Figures relative to the chassis 19, the lever 48 is pushed upwards. This causes the first arm 45 to come into contact with enclosing a circuit on the PCBA as the contact tabs 47 are always in contact with the PCBA creating the other contact point for the circuit. At this stage of the actuator lever 49 rests in a bottom section of the ratchet profile 42.

In the second switching mode of the switch assembly 40, i.e. when the dial grip 12 is further depressed during dose delivery thereby causing relative rotation of the encoder ring 41 with respect to the chassis 19, the actuator lever 49 rides over the ratchet profile 42 of the encoder ring 41. This alternately deflects the second arm 46 such that the gap between the the second arm 46 and the second electrical contact is closed as the actuator lever rides over the peak portions of the ratchet profile 42 and is opened again as the actuator lever 49 rides over a bottom section of the ratchet profile 42. This second switch operation mode of the switch assembly 40 is preferably used to wake up the rotary sensor 120 as described above.

In other words, when the encoder ring 41 starts to rotate the actuator lever 49 will be pushed up as seen in the Figures thereby causing the second arm 46 to come into contact with enclosing the circuit on the PCBA each time the actuator lever 49 passes over the peak of the ratchet profile 42. The first arm 45 remains engaged continuously throughout the rotational motion of the encoder ring 41.

A fourth embodiment of a switch assembly 50 is depicted in FIGS. 5*a* to 5*i*.

In the switch assembly 50, the arrangement of the button module 11, the dial grip 12 and the module chassis 19 with the PCBA of the electronic control unit 110 is as well as the arrangement of an encoder ring 51 with a ratchet profile 52 and a surrounding guiding surface 53 is identical to the switch assembly 40. In addition, the relative movements of the module chassis 19 and the encoder ring 51 during the different operational stages of the drug delivery device 1 are identical. In a similar manner as in the switch assembly 30, a bridge 54 is provided in an opening of the chassis 19 permitting limited axial movement of the bridge 54 with respect to the chassis 19.

The distal surface of the PCBA is provided with a first electrical contact, the second electrical contact and at least one third electrical contact in a similar manner as described above with respect to the switch assembly 40 (not shown in FIGS. 5*a* to 5*i*).

The switch assembly 50 further comprises a first spring element 55 which is arranged and held on the chassis 19. The first spring element 55 comprises a first arm 56 which is arranged to abut a portion of the bridge 54. For this purpose, the first arm 56 may be bent distally. Further, the first spring element 55 comprises a biasing arm 57 which is also bent distally and which is arranged on an opposite side of the first spring element 55 in the exemplary embodiments shown in the Figures. Still further, the first spring element 55 comprises a contact tab 58 which is bent proximally to be biased in electrical connection with the third electrical contact on the PCBA. The bridge 54 carries a second spring element 59 comprising an arm which is biased towards the PCBA thereby establishing an electrical connection with the second electrical contact. The second spring element 59 further comprises a second arm 60 with an actuator 61 which has a tooth-like protrusion facing distally to abut the ratchet profile 52 of the encoder ring 51.

In the default state, the contact tab 58 abuts the third electrical contact and the second arm 60 abuts the second electrical contact, whereas the first arm 56 is axially spaced from the first electrical contact. Further, the biasing arm 57 and the second arm 60 are axially spaced from each other. Thus, in the default state, neither the first electrical contact nor the second electrical contacts is connected to the third electrical contact via the first and second spring elements 55, 59.

In the first switching mode of the switch assembly 50, i.e. when the dial grip 12 is depressed, the resulting axial movement of the chassis 19 relative to the encoder ring 51 and, thus, the bridge 54 results in the bridge 54 deflecting the first arm 56 in the proximal direction (upwards in the Figures) such that the first arm 56 abuts the first electrical contact on the PCBA. Closing the electrical connection between the first electrical contact and the third electrical contact via the deflected first arm 56 in the first switch operation mode of the switch assembly 50 is preferably used to wake up the communication unit 140 as described above.

In other words, when the encoder ring 51 moves upwards as seen in the figures relative to the chassis 19 where the rich component 54 and the first spring element 55 are located, the bridge 54 is being pushed upwards as seen in the figures. This causes the first arm 56 of the first spring element 55 to come into contact with and closing the circuit on the PCBA as the contact tab 58 is always in contact with the PCBA. At this stage the second switch inside the bridge 54 rests in a bottom section of the ratchet 52.

In the second switching mode of the switch assembly 50, i.e. when the dial grip 12 is further depressed during dose delivery thereby causing relative rotation of the encoder ring 51 with respect to the chassis 19, the actuator 61 rides over the ratchet profile 52 of the encoder ring 51. This alternately deflects the second arm 60 via the actuator 61 such that the gap between the the second arm 60 and the biasing arm 57 is closed as the actuator 61 rides over the peak portions of the ratchet profile 52 and is opened again as the actuator 61 rides over a bottom section of the ratchet profile 52. This second switch operation mode of the switch assembly 50 is preferably used to wake up the rotary sensor 120 as described above.

In other words, when the encoder ring 51 starts to rotate the rotational switch formed by the second spring element 59 will will be pushed up as seen in the figures and come into contact with the biasing arm 57 of the first spring element 55 and thereby closes a circuit on the PCBA each time the free end 61 of the second arm 60 passes over a peak of the ratchet profile 52. The first axial switch of the switch assembly 50 remains engaged continuously throughout the rotational motion of the encoder ring 51.

Although described mainly with respect to a drug delivery device having a similar working principle as the device disclosed in EP 2 890 435, the electronic system is applicable to any other type of drug delivery device having component parts performing a relative axial and/or rotational movement in defined conditions or states.

REFERENCE NUMERALS

1 device
10 housing
11 button module
12 dial grip
13 dosage window
14 container/container receptacle
15 needle
16 inner needle cap
17 outer needle cap
18 cap
19 module chassis
20 switch assembly
21 encoder ring
22 ratchet profile
23*a-d* electrical contact
24 lever
25 first end of lever 24
26 second end of lever 24
27 first spring arm
28 second spring arm
30 switch assembly
31 encoder ring
32 bridge
33*a-c* electrical contact
34 first spring element
34*a* first end
34*b* second end
35 second spring element
36 first arm
37 second arm
38 tooth-like protrusion (actuator)
40 switch assembly
41 encoder ring
42 ratchet profile
43 guiding surface
44 annular metal pressing
45 first arm
46 second arm
47 contact tab
48 lever
49 actuator lever

50 switch assembly
51 encoder ring
52 ratchet profile
53 guiding surface
54 bridge
55 first spring element
56 first arm
57 biasing arm
58 contact tab
59 second spring element
60 second arm
61 actuator arm
100 electronic system
110 electronic control unit (PCBA)
120 encoding and motion sensing unit
130 use detection unit
140 communication unit
150 electrical power supply

The invention claimed is:

1. A switch assembly for an electronic system of a drug delivery device, the switch assembly comprising:

a chassis supporting a printed circuit board assembly (PCBA) which has a distal surface comprising at least a first electrical contact, a second electrical contact, and a third electrical contact;

a ring having an annular ratchet profile; and a first electrically conductive and elastically deformable arm) and a second electrically conductive and elastically deformable arm, wherein the chassis is configured to move axially relative to the ring from a first axial position to a second axial position during a first switch operation mode, wherein the chassis and the ring are configured such that the ring rotates relative to the chassis during a second switch operation mode, wherein the first arm is arranged such that an axial movement of the chassis towards the ring during the first switch operation mode closes an electrical connection between the first electrical contact and the first arm, and wherein the ratchet profile of the ring is located facing proximally towards the distal surface of the PCBA such that an actuator guided on the ratchet profile at least during the second switch operation mode elastically deforms the second arm thereby alternately opening and closing an electrical connection between the second electrical contact and the third electrical contact via the second arm.

2. The switch assembly according to claim 1, wherein the first switch operation mode occurs during a transition from a dose setting operation to a dose delivery operation of the drug delivery device, or when the chassis is pressed in a zero unit dose dialled condition of the drug delivery device.

3. The switch assembly according to claim 1, wherein the second switch operation mode occurs during a dose delivery operation of the drug delivery device.

4. The switch assembly according to claim 1, wherein the actuator is a lever having a first end hinged to the chassis and a free second end opposite the first end which contacts the ring during the first and second switch operation modes.

5. The switch assembly according to claim 4, wherein the free second end of the lever is axially spaced from the ratchet profile when the chassis is in the first axial position, contacts at least one of a plurality of bottom sections of the ratchet profile and elastically deflects the first arm when the chassis is in the second axial position, and alternates between contacting the bottom sections and peak sections of the ratchet profile, and elastically deflects the second arm during the second switch operation mode.

6. The switch assembly according to claim 4, wherein the electrical connection between the first arm and the first electrical contact is open when the chassis is in the first axial position, and is closed when the chassis is in the second axial position, and wherein the electrical connection between the second arm and the second electrical contact is open in the first and the second axial positions and is alternately closed during the second switch operation mode when the free second end of the lever contacts peak sections of the ratchet profile.

7. The switch assembly according to claim 1, further comprising a bridge holding a first electrically conductive spring element and a second electrically conductive spring element, wherein the bridge is interposed between the ring and the PCBA such that the spring elements bias the bridge away from the PCBA and towards the ring, and wherein the first arm is a free end of the first spring element and the second arm is a free end of the second spring element.

8. The switch assembly according to claim 7, wherein the first spring element is a metal pressing comprising three free ends, wherein a first free end of the three free ends is permanently biased in abutment with the third electrical contact, a second free end of the three free ends is held in the bridge in a position allowing abutment with the second arm if the second arm is elastically deflected a predefined degree towards the second free end the first arm, and a third free end of the three free ends constitutes the first arm which is held in the bridge in a position allowing abutment with the first electrical contact if the first free end is deflected a predefined distance towards the second free end upon axial movement of the chassis towards the ring during the first switch operation mode.

9. The switch assembly according to claim 7, wherein the second spring element is a metal pressing comprising two free ends, wherein a first free end of the two free ends is permanently biased in abutment with the second contact, and a second free end of the two free ends forms the second arm which carries the actuator.

10. The switch assembly according to claim 9, wherein the actuator is guided on the ratchet profile at least during the second switch operation mode such that the second arm alternates between contacting bottom sections and peak sections of the ratchet profile thereby alternately elastically deflecting the second arm towards the first spring element.

11. The switch assembly according to claim 1, wherein the first arm and the second arm are free ends on a single annular metal pressing that is interposed between the chassis and the PCBA in a position permitting at least one elastically deformable contact tab of the pressing to abut the third electrical contact of the PCBA.

12. The switch assembly according to claim 11, wherein the annular metal pressing further comprises a lever located such that the lever abuts a proximally facing annular guiding surface of the ring when a predefined axial movement of the chassis towards the ring occurs during the first switch operation mode, thereby deflecting the first arm (45) to abut the first electrical contact.

13. The switch assembly according to claim 11, wherein the annular metal pressing further comprises an actuator lever located such that the actuator lever abuts the proximally facing ratchet profile of the ring at least after the first switch operation mode, wherein the actuator lever is guided on the ratchet profile (42) and alternates between contacting bottom sections and peak sections of the ratchet profile at least during the second switch operation mode such that the actuator lever alternately elastically deforms the second arm thereby opening and closing an electrical connection between the second electrical contact and the second arm.

14. The switch assembly according to claim 1, further comprising:

a first electrically conductive spring element; and a bridge holding a second electrically conductive spring element, wherein the bridge is arranged in the chassis interposed between the ring and a biasing arm such that the bridge (54) is held in abutment with the ring by the biasing arm and is axially displaceable relative to the chassis against the bias of the biasing arm upon axial movement of the chassis towards the ring during the first switch operation mode.

15. The switch assembly according to claim 14, wherein the first arm is part of the first electrically conductive spring element, wherein the first electrically conductive spring element comprises a contact tab held in the chassis in a position permitting the contact tab to abut the third electrical contact of the PCBA, and wherein the bridge is arranged in the chassis such that the bridge elastically deflects the first arm upon axial movement of the chassis towards the ring during the first switch operation mode thereby closing an electrical connection between the first electrical contact and the first arm.

16. The switch assembly according to claim 14, wherein the second spring element is a metal pressing comprising two free ends, wherein a first free end of the two free ends is biased in abutment with the second contact at least during the second switch operation mode, and a second free end of the two free ends forms the second arm that carries the actuator.

17. The switch assembly according to claim 16, wherein the actuator is guided on the ratchet profile at least during the second switch operation mode such that the second arm alternates between contacting bottom sections and peak sections of the ratchet profile thereby alternately elastically deflecting the second arm towards the first spring element.

18. A drug delivery device comprising:

an electronic system including a switch assembly that comprises a chassis supporting a printed circuit board assembly (PCBA) which has a distal surface comprising at least a first electrical contact, a second electrical contact, and a third electrical contact, a ring having an annular ratchet profile, and a first electrically conductive and elastically deformable arm) and a second electrically conductive and elastically deformable arm, wherein the chassis is configured to move axially relative to the ring from a first axial position to a second axial position during a first switch operation mode, wherein the chassis and the ring are configured such that the ring rotates relative to the chassis during a second switch operation mode, wherein the first arm is arranged such that an axial movement of the chassis towards the ring during the first switch operation mode closes an electrical connection between the first electrical contact and the first arm, and wherein the ratchet profile of the ring is located facing proximally towards the distal surface of the PCBA such that an actuator guided on the ratchet profile at least during the second switch operation mode elastically deforms the second arm (28, 37, 46, 60) thereby alternately opening and closing an electrical connection between the second electrical contact and the third electrical contact via the second arm;

a dose setting and drive mechanism configured to perform a dose setting operation for setting a dose to be delivered by the drug delivery device and a dose delivery operation for delivering the set dose, the dose setting and drive mechanism comprising the ring; and a button module comprising an electronic control unit (110) on the PCBA, a rotary sensor, a communication unit with a wireless communication interface for communicating with another device, and a use detection unit comprising the switch assembly, wherein the electronic control unit is configured to control an operation of the electronic system.

19. The drug delivery device according to claim 18, wherein the button module and the dose setting and drive mechanism are configured such that a dose dial assembly rotates relative to the button module during the dose delivery operation but does not rotate relative to the button module during the dose setting operation and that the button module moves axially relative to the dose dial assembly during the transition from the dose setting operation to the dose delivery operation, or when the button module is pressed in a zero unit dose dialled condition, wherein the electronic system is configured such that the communication unit is switched from a sleeping mode into an operation mode inducing the communication unit (140) to initiate a manual synchronization and/or a pairing with another device upon closing an electrical connection between the first electrical contact and the first arm during the first switch operation mode, and wherein the electronic system is configured such that the rotary sensor is switched from a sleeping mode into an operation mode inducing the rotary sensor (120) to initiate a motion detection upon closing an electrical connection between the second electrical contact and the third electrical contact via the second arm during the second switch operation mode.

20. The drug delivery device according to claim 18, further comprising a container receptacle which is permanently or releasably connected to the dose setting and drive mechanism, and which is adapted to receive a container containing a medicament.

* * * * *